US012558374B2

(12) United States Patent
Modak et al.

(10) Patent No.: US 12,558,374 B2
(45) Date of Patent: Feb. 24, 2026

(54) BOTANICAL FILM-FORMING ACNE COMPOSITIONS

(71) Applicant: The Trustees of Columbia University in the City of New York, New York, NY (US)

(72) Inventors: Shanta M. Modak, River Edge, NJ (US); Chathuranga C. De Silva, Cliffside Park, NJ (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 18/379,598

(22) Filed: Oct. 12, 2023

(65) Prior Publication Data

US 2024/0374633 A1      Nov. 14, 2024

Related U.S. Application Data

(60) Continuation of application No. 17/178,692, filed on Feb. 18, 2021, now abandoned, which is a division of application No. 16/415,339, filed on May 17, 2019, now abandoned.

(60) Provisional application No. 62/684,030, filed on Jun. 12, 2018.

(51) Int. Cl.
| | |
|---|---|
| *A61K 31/327* | (2006.01) |
| *A61K 9/00* | (2006.01) |
| *A61K 9/06* | (2006.01) |
| *A61K 9/107* | (2006.01) |
| *A61K 31/192* | (2006.01) |
| *A61K 33/30* | (2006.01) |
| *A61K 36/28* | (2006.01) |
| *A61K 36/886* | (2006.01) |
| *A61K 47/38* | (2006.01) |
| *A61P 17/10* | (2006.01) |

(52) U.S. Cl.
CPC ............ *A61K 33/30* (2013.01); *A61K 9/0014* (2013.01); *A61K 9/06* (2013.01); *A61K 9/107* (2013.01); *A61K 31/192* (2013.01); *A61K 31/327* (2013.01); *A61K 36/28* (2013.01); *A61K 36/886* (2013.01); *A61K 47/38* (2013.01); *A61P 17/10* (2018.01)

(58) Field of Classification Search
CPC ...................................................... A61K 33/30
See application file for complete search history.

(56) References Cited

U.S. PATENT DOCUMENTS

| | | | |
|---|---|---|---|
| 7,951,840 B2 | 5/2011 | Modak | |
| 2005/0281762 A1* | 12/2005 | Modak | A61K 31/315 424/70.13 |
| 2009/0004122 A1* | 1/2009 | Modak | A01N 65/22 424/59 |
| 2010/0047295 A1 | 2/2010 | Giagnorio | |
| 2010/0247476 A1 | 9/2010 | Von Thaden | |
| 2012/0058061 A1 | 3/2012 | Nguyen | |
| 2013/0230609 A1 | 9/2013 | Modak | |
| 2015/0265666 A1 | 9/2015 | Modak | |
| 2016/0374352 A1* | 12/2016 | Modak | A61K 31/155 424/54 |

FOREIGN PATENT DOCUMENTS

| | | |
|---|---|---|
| CN | 101778620 | 7/2010 |
| CN | 104994878 | 10/2015 |
| KR | 20020078709 | * 10/2002 |
| WO | 2010109420 | 9/2010 |

OTHER PUBLICATIONS

Croda. Incroquat Behenyl TMS-50 (Year: 2004).
International Search Report dated Jul. 19, 2019, issued in PCT/US2019/032832.

* cited by examiner

*Primary Examiner* — Sarah Alawadi
(74) *Attorney, Agent, or Firm* — FULLER IP LAW LLC; Rodney J. Fuller; Scott H. Blackman

(57) ABSTRACT

The present technology relates to botanical film-forming compositions useful for the treatment of acne related skin disorders, as well as methods of treating such disorders. The compositions herein are advantageous in that they treat acne related skin disorders quickly and with minimal irritation and side effects.

3 Claims, 1 Drawing Sheet

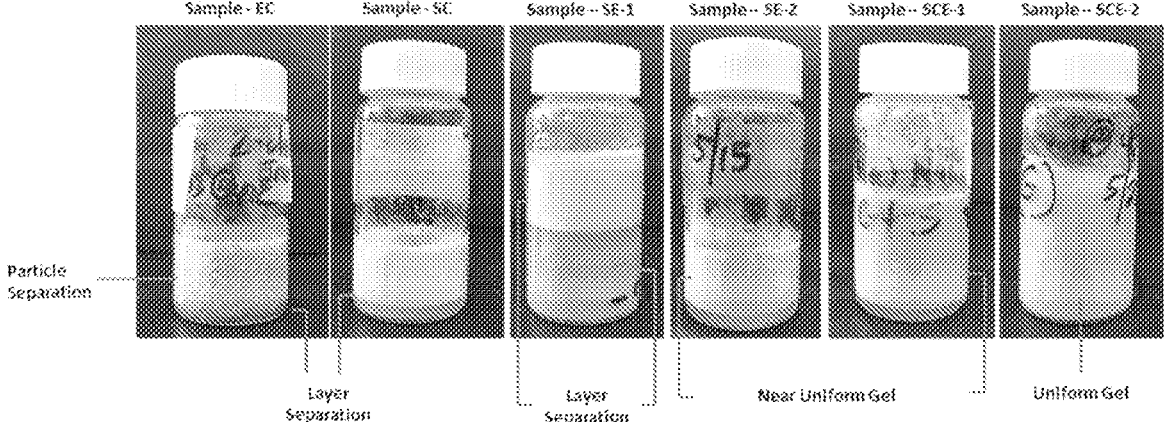

BOTANICAL FILM-FORMING ACNE COMPOSITIONS

CROSS-REFERENCE TO RELATED APPLICATIONS

This application is a Continuation of U.S. patent application Ser. No. 17/178,692 filed Feb. 18, 2021, entitled "Botanical Film-Forming Acne Compositions," which is a Divisional Application of U.S. patent application Ser. No. 16/415,339, filed on May 17, 2019, entitled "Botanical Film-Forming Acne Compositions," which claims the benefit of U.S. Provisional Application No. 62,684,030 filed Jun. 12, 2018, the contents of each of which are incorporated by reference in their entirety.

BACKGROUND

The present technology relates to compositions suitable for treating acne related skin disorders.

Acne, also known as acne vulgaris, is a chronic inflammatory disease of the skin, found in 80% of adolescents and young adults. It is a skin condition characterized by primary lesions on the face, chest, and back, which form when the skin pores become clogged with oil, dead skin cells, and bacteria. Acne often occurs when the sebaceous glands overproduce sebum. A clogged pore can also accumulate dirt, debris, and bacteria. When the blockage or plug (comedone) ruptures, the material inside can spread to surrounding skin. The resulting skin condition with sebum enrichment is prone to the anaerobic growth of *Propionibacterium acnes*, which is the main causative microorganism in acne. In addition, *Staphylococcus epidermidis* and *Staphylococcus aureus* can be present in acne lesions. Proliferation of these microorganisms, mainly *P. acnes*, leads to inflammatory lesions and severe acne.

Current methods that are used to reduce sebum production, unclog pores, or treat acne include caustic agents that can further lead to skin irritation or can result in dry and flaky skin. Acne also causes significant psychological morbidity in affected patients.

Some treatments have been introduced to decrease the aesthetic and psychological problems caused by acne. Products currently available for the treatment of acne include systemic and topical treatments. The topical application of therapeutic agents has been found to be more feasible than hormonal treatment and laser therapy. Active agents currently used for topical therapy are retinoic acid and derivatives, benzoyl peroxide salicylic acid, and antibiotics. While it has been noted that salicylic acid is the least deleterious agent among all other topical agents, continued use of these agents can cause adverse effects, e.g. skin irritation, redness and bacterial resistance. Furthermore, certain formulations can take a significant amount of time, up to 6 weeks, to improve skin. Herbs and naturally derived compounds in topical acne treatments have received interest as they seem to have fewer adverse effects than synthetic agents. However, these agents tend to be slow in acting, and therefore high concentrations are needed for efficacy; this can be toxic.

Previously, we have developed anti acne formulations containing salicylic acid based on our patented technology (U.S. Pat. Nos. 7,563,461 and 7,879,365) to treat acne related skin disorders. This 4 step treatment involves the use of a cleanser, a toner, a lotion and a spot cream to be applied twice daily. This treatment has shown significant, visible improvement in acne affected skin during regular use of 4-6 weeks.

However, research has shown that, like most competing anti-acne topical products currently available, the 4 step treatment can be time consuming, and therefore patients may not adhere to this routine.

Thus, there is an ongoing need for new and innovative therapies that are fast acting, come from natural sources, are simple to use and cause minimal irritation.

SUMMARY

In certain embodiments, the present technology is directed to a composition suitable for treating an acne related skin disorder, comprising:

(a) 0.1 to 1% w/w hydroxypropyl methylcellulose stearoxy ether (hydrophobically modified hydroxypropyl methylcellulose) (HPMCSE polymer);

(b) 0.1 to 1% w/w soluble zinc salt, wherein the soluble zinc salt is zinc gluconate, zinc lactate, zinc acetate, zinc citrate or any combination thereof;

(c) an emulsifying agent, wherein the emulsifying agent comprises: (1) 0.1 to 5% w/w of one more of: behentrimonium methosulfate, cetyl alcohol, stearyl alcohol, butylene glycol, or a cetyl alcohol and butylene glycol blend (referred to as BTMSCB) or any combination thereof; and (2) 0.1 to 5% w/w nonionic self-emulsifying wax (e.g., Polawax™); and (d) 0.5 to 2% w/w salicylic acid, or 0.5 to 10% w/w benzoyl peroxide, or a combination thereof.

In other embodiments, the compositions herein further comprise chitosan, e.g., 0.1 to 1%; and cellulose polymer, e.g. hydroxyethyl cellulose, hydroxyl propyl methyl cellulose, methyl cellulose, polyquaternium 10, or any combination thereof; in amounts of, e.g., 0.1 to 3%.

In other embodiments, the compositions herein further comprise calendula oil or extract, in amounts of, e.g., 0.1 to 20% or 0.1 to 2%; or aloe gel or extract, in amounts of, e.g., 0.1 to 5%, 0.1 to 50%, or any combination thereof.

In other embodiments, the compositions herein further include emollient solvent, wherein the emollient solvent is 1,3-propanediol (for example, that available under the trade name Zemea® from DuPont Tate & Lyle Bio Products Company, LLC of Loudon, TN, USA), glycerin, caprylil capryl triglyceride, butylene glycol, octanediol, decanediol, benzyl alcohol, ethyl hexyl glycerin, farnesol or any combination thereof, in amounts, of, e.g., 0.5 to 10% w/w.

In other embodiments, the compositions herein further comprise a botanical; in various embodiments, the botanical can be, for example, orange oil, 0.05 to 0.2% w/w rosemary oil, 0.01 to 0.1% w/w vetiver oil, 0.01 to 0.1% w/w red sandalwood powder or extract, 0.2 to 1% w/w pomegranate oil or extract, 0.3 to 1% w/w grapefruit seed extract, 0.3 to 1% w/w lemon extract, 0.2 to 3% w/w tea tree oil, 0.2 to 2% w/w *arnica* oil, 0.2 to 2% w/w licorice extract, 0.2 to 2% w/w frankincense oil, 0.01 to 2% w/w *helichrysum* oil, 0.01 to 2% w/w geranium oil, 0.01 to 2% w/w myrrh oil, 0.01 to 2% w/w *neroli* oil, 0.01 to 1% w/w Withania somnifera flower extract, 0.01 to 1% w/w manjistha (*Rubia cordifolia*) extract, 0.5 to 5% onion extract, or any combination thereof.

In various embodiments, the compositions herein comprise glycolic acid, lactic acid, benzoic acid or a combination thereof, in amounts of 0.1 to 1% each—that is, for a total possible amount of 3% of such acids.

In other embodiments, the compositions herein further comprise an additional ingredient, including but not limited to: a solvent or solubilizing agent; a surfactant water, alcohol, sorbitan mono laurate (e.g., Tween® 20), sorbitan mono oleate (e.g., Tween® 80), sorbitan oleate decylglucoside, sorbitan sugar (e.g., Poly Suga® mulse), caprylil capryl glucoside, PEG 40 hydrogenated castor oil, trideceth-9 propylene glycol (e.g., Symrise® solubilizer 660352), cocoamidopropyl betaine, water or any combination thereof.

In other embodiments, the compositions herein further comprise an essential oil or constituent (ingredient) thereof, or a botanical extract, including but not limited to: lavender oil, chamomile oil, basil oil, thyme oil, thymol, menthol, orange oil, vetiver oil, bakuchiol, jojoba oil, coconut oil, sun flower oil, safflower oil, almond oil, bee honey, white tea extract, green tea extract, resveratrol or any combination thereof.

In other embodiments, the compositions herein further comprise a preservative, in amounts of, e.g., 0.1 to 1%. In various embodiments, the preservative is chlorhexidine (for example, chlorhexidine gluconate), benzalkonium chloride, phenoxyethanol, phenyl ethanol or any combination thereof.

In other embodiments, the compositions herein further comprise an antioxidant, e.g., Vitamin E, Vitamin C or any combination thereof.

In other embodiments, the present technology is directed to methods of treating an acne related skin disorder, comprising contacting any of the compositions described herein with the skin.

In other embodiments, the present technology is directed to a method of treating an acne related skin disorder, comprising the following steps:
- (a) dissolving soluble zinc salt, aloe powder, lactic acid and glycolic acid in water at a temperature of 50 to 60° C.;
- (b) optionally adding a thickener or surfactant;
- (c) adding an emulsifying agent, the emulsifying agent comprising behentrimonium methosulfate, cetyl alcohol and butylene glycol (BTMSCB) and nonionic self-emulsifying wax; and mixing until dissolved;
- (d) allowing the mixture to cool down to 30 to 40° C.;
- (e) adding HPMCSE polymer gel, chitosan gel and calendula extract;
- (f) mixing to obtain a creamy gel (Phase A);
- (g) combining salicylic acid and one or more botanical extracts or oils in a solvent, and mixing (Phase B);
- (h) combining Phase A and B to obtain an acne composition; and
- (i) contacting the acne composition with skin.

BRIEF DESCRIPTION OF THE DRAWING

The FIGURE depicts relative stability of the formulations (samples EC, SC, SE-1, SE-2, SCE-1, SCE-2) as shown by pictures taken after 7 days at 40° C.

DETAILED DESCRIPTION

All percentages expressed herein are by weight unless otherwise indicated.

In certain embodiments, the technology herein is directed to a 2 step treatment for treating skin disorders related to acne using a film forming gel containing salicylic acid and botanicals.

As used herein, the terms "acne related skin disorders" and "skin disorders related to acne" and interchangeable and mean any skin condition caused by a buildup of dead skin cells, bacteria or dried sebum that blocks the hair follicles in the skin, or causes blackheads (open comedones), whiteheads (closed comedones), pimples (papules), cysts or abesses in the skin.

As used herein, "essential oil" (EO) is a volatile oil obtained from a plant or an animal source that comprises one or more active agent (also referred to herein as an Isolated Component or "IC" or "constituent" or "ingredient") which can be, for example but not by way of limitation, a monoterpene or sesquiterpene hydrocarbon, alcohol, ester, ether, aldehyde, ketone, or oxide. Essential oils are commonly extracted by distillation, expression, extraction, resin tapping, wax embedding or cold pressing. Isolated components generally fall into the following categories: acids, alcohols (e.g., monoterpenols or sesquiterpenols), aldehydes, coumarins, esters, ketones, lactones, terpenes (e.g., monoterpenes or sesquiterpenes), oxides, or phenols.

Throughout this present disclosure, when referring to a natural (plant or animal) source of oil, for example, "lemon oil" or "emu oil," this means the same thing as referring to the essential oil; with the exception that where essential oil is not commercially available, absolute oil is used.

As used herein, "botanical extract" means a composition from a plant source (a botanical) that is prepared by soaking the botanical in a solvent (e.g. water or alcohol). A botanical extract refers to the resultant liquid, which contains the essential oil with the solvent. As described in Examples and data herein, the terminology "(100%/oil)" denotes 100% extract or oil.

Botanicals and naturally derived compounds in topical acne treatments, have received considerable interest as they have fewer adverse effects than synthetic agents. However, these agents are slow acting and therefore high concentrations are needed to be efficacious which can be toxic. Our earlier studies with botanicals indicate that a combination treatment with botanicals and synthetic agents can be more effective than the application of a single product to inactivate bacteria.

We describe the development of a unique film forming gel containing zinc, salicylic acid and botanicals (FGZB) formulation to treat mild and moderate acne.

In certain embodiments, FGZB includes ingredients having varied and therapeutic properties in combination. The unique compositions described herein can inhibit the growth of microbes that cause numerous conditions including acne, itching, erythema, and scaling. The compositions can also result in reduction in the numbers of papules and pustules; and can also be effective in controlling sebum secretion. Additionally, in certain embodiments the compositions herein can remain on the skin for longer period and release the actives continuously into the skin upon application.

In certain embodiments, the antibacterial actives in the formulations are combinations of one or more botanicals and salicylic acid. This unique technology, among other characteristics, can: (i) enhance the antimicrobial efficacy of salicylic acid; (ii) moisturize the skin rather than drying and irritating it while staying non-greasy, and (iii) create a long lasting barrier film on the skin preventing the passage of irritants and bacteria, and at the same time inactivating skin bacteria that cause acne lesions.

In certain embodiments, a composition herein comprises one or more of the following ingredients (each described in turn):
- (a) 0.1 to 1% w/w hydroxypropyl methylcellulose stearoxy ether. This is a hydrophobically modified hydroxypropyl methylcellulose polymer (HPMCSE polymer) that can form a unique film forming hydrophobic/ hydrophilic gel in water, and can provide a silky smooth feel on the skin upon application.

(b) 0.1 to 1% soluble zinc salts. Exemplary zinc salts include zinc gluconate, zinc lactate, zinc acetate, zinc citrate and combinations thereof. Zinc salts are anti-irritant and anti-inflammatory, and when combined with the film forming HPMCSE polymer forms barrier matrix containing zinc which can precipitate the proteins in the inflammatory papules and pustules and therefore can reduce their size and appearance. Furthermore, this matrix can prevent the passage of irritants and bacteria and at the same time inactivating skin bacteria causing acne lesions.

(c) 0.1 to 5% emulsifying agents. Such emulsifying agents can comprise any of the following: 1) BTMSCB which is a blend of Behentrimonium Methosulfate (and) Cetyl Alcohol (and) Butylene Glycol, an elegant vegetable based conditioning emulsifier; or 2) 0.1 to 3% of a nonionic self-emulsifying wax, e.g., those available under the trade name Polawax™ and available from Croda Inc. (Snaith, East Yorkshire, United Kingdom). Other emulsifiers include those available under the trade name Ritabate® from Rita Corporation (Crystal Lake, IL, USA), and polyquaternium emulsifiers available under the trade name Ucare® from Univar Solutions (Downers Grove, IL, USA). In certain embodiments, the composition comprises a total of 0.2 to 10% w/w emulsifying agents, for example, 0.1 to 5% of the options for 1) listed above, and 0.1 to 5% of the nonionic self-emulsifying wax of 2) listed above.

In certain embodiments, it has been found that combined use of a, b, c ingredients in the formulation results in a stable film forming gel (FGZ) which is non-sticky, non-greasy, with emollient and moisturizing properties. When active ingredients e.g. salicylic acid and botanicals are incorporated in FGZ, and applied on the skin, they are released in a sustained manner for a prolonged period inhibiting bacterial growth and reducing acne related skin disorders.

(d) 0.2 to 2% of an alpha hydroxy acid e.g. salicylic acid, lactic acid, glycolic acid or any combination thereof, which can help to regenerate, or peel off, the top layer of skin, remove dead skin cells and unclogging pores in the process, thus preventing lesions and allowing for new clear skin to form.

In certain embodiments, the FGZ containing salicylic acid can further comprise any of the following (1)-(9):

(1) 0.1 to 1% chitosan which is a natural film forming polysaccharide polymer with antimicrobial and wound healing properties;

(2) 0.1 to 3% cellulose polymers (which can act as thickening agents) that can comprise any of the following: hydroxyethyl cellulose, hydroxyl propyl methyl cellulose (for example, that sold under the trade name Methocel™ and available from Dow Chemical Co. of Midland, MI), methyl cellulose, polyquaternium 10 (quaternized hydroxyl ethyl cellulose), hydroxypropyl methyl-cellulose stearoxy ether (for example, that sold under the trade name Sangelose® and available from Daido Chemical Corporation of Osaka, Japan), or any combinations thereof;

(3) a botanical blend that can comprise any of the following: rosemary oil, (0.05 to 0.2%) and vetiver oil (0.01 to 0.1%), red sandalwood paste/extract (0.01 to 0.1%), orange oil (0.1 to 0.5%), plant based 1,3 propanediol (1 to 10%), benzyl alcohol (0.5 to 2%) and any combination thereof. This botanical blend, when used in FGZ+salicylic acid formulation, enhances the anti-bacterial activity and reduces skin irritation;

(4) 0.1 to 0.5% or 0.1 to 5% calendula oil or extract, 0.1 to 0.5% or 0.1 to 5% aloe vera gel or extract or a combination thereof, which reduces inflammation, soothes the skin, relieves the itching, irritation and burning sensation;

(5) 0.3 to 7% emollient solvents, which can be any of the following: 1,3 propanediol, glycerin, caprylil capryl triglyceride, butylene glycol, octanediol, decanediol, benzyl alcohol, octoxyglycerin, farnesol or any combination thereof.

(6) one or more alpha hydroxy acids or fruit acids, which can be any of the following: glycolic acid, lactic acid, benzoic acid or any combination thereof;

(7) one or more essential oils or botanical extracts, or constituents thereof (that is, constituents of essential oils or botanical extracts), which can be any of the following: pomegranate oil or extract (0.3 to 1%), Grapefruit seed extract (0.3 to 1%), lavender oil, chamomile oil, basil oil, thyme oil, thymol, menthol, Farnesol, bakuchiol, grapefruit seed extract, jojoba oil, white tea extract, green tea extract, resveratrol or any combination thereof. These ingredients have antibacterial and anti-inflammatory properties;

(8) one or more solvents e.g. water, alcohol, sorbitan mono laurate (e.g., Tween® 20), sorbitan mono oleate (e.g., Tween® 80), sorbitan oleate decylglucoside, sorbitan sugar (e.g., Poly Suga® mulse), caprylil capryl glucoside, mixture of PEG 40 hydrogenated castor oil, trideceth-9 propyleneglycol (e.g., Symrise® solubilizer 660352), Peg 40 hydrogenated castor oil, trideceth-9, water (e.g., Symrise® solubilizer 611674)

(9) a preservative, e.g., chlorhexidine, benzalkonium chloride, phenoxyethanol, phenyl ethanol or any combination thereof (0.1 to 1%).

In various embodiments, a composition herein can comprise any of a number of additional ingredients, including but not limited to the following: retinol (also known as Vitamin A1), or a natural alternative to retinol, for example, a bakuchiol compound available under the trade name Sytenol® from Sytheon Ltd. (Boonton, NJ, USA); one or more poloxamers—that is, nonionic triblock copolymers composed of a central hydrophobic chain of chain of poly-oxypropylene (poly(propylene oxide)) flanked by two hydrophilic chains of polyoxyethylene (poly(ethylene oxide)), and which are available under the trade name Pluronic® from BASF Corporation (Ludwigshafen, Germany); anti-irritant or anti-itch or antihistamic compounds, for example, synthetic avenanthramide available under the trade name SymCalmin® from Symrise AG (Holzminden, Germany); Vitamins, whether or not considered to be antioxidants, for example, Vitamin A, Vitamin C, Vitamin E or Vitamin B, e.g., Pro Vitamin B-5 compounds available under the trade name Ritapan® from Rita Corporation (Crystal Lake, IL, USA); or a thickener, e.g., one available under the trade name Incromine™ from Croda Personal Care (Snaith, East Yorkshire, United Kingdom); or hair enhancing compositions such as that available under the trade name Incroquat™ Behenyl TMS from Croda Personal Care (Snaith, East Yorkshire, United Kingdom);

Example 1

Development of Stable FGZB Formulation

The following formulations were prepared, including varying amounts of emulsifiers, HPMCSE polymer(S), Chitosan (C) and combinations thereof. These formulations were evaluated for film formation and stability.

Formulation Sample EC

| Ingredient | % (w/w) |
| --- | --- |
| Salicylic acid | 2 |
| Base ingredient | |
| Deionized Water | Q.S. to 100 |
| Zinc gluconate | 0.2 |
| Zinc lactate | 0.2 |
| Aloe powder | 0.2 |
| Glycolic acid | 0.5 |
| Lactic acid | 0.2 |
| BTMSCB emulsifier (E) | 2.5 |
| Polawax ™ emulsifier (E) | 2.5 |
| Chitosan (C) | 0.15 |
| Calendula extract | 0.2 |
| Alcohol denatured | 10 |
| 1,3 propanediol | 2 |
| Caprylil capril triglyceride | 2 |
| Ethyl hexyl glycerin | 1 |
| Decanediol | 0.5 |
| Bisabolol | 0.1 |
| Pomegranate oil | 0.5 |
| Rosemary oil | 0.1 |
| Thymol | 0.1 |
| Menthol | 0.1 |
| Orange oil | 0.2 |
| Vetiver oil | 0.02 |
| Resveratrol | 0.5 |
| Red sandalwood extract | 0.1 |
| Chlorhexidine gluconate | 0.05 |

Formulation Sample SC

| Ingredient | % (w/w) |
| --- | --- |
| Salicylic acid | 2 |
| Base ingredient | |
| Deionized Water | Q.S. to 100 |
| Zinc gluconate | 0.2 |
| Zinc lactate | 0.2 |
| Aloe powder | 0.2 |
| Glycolic acid | 0.5 |
| Lactic acid | 0.2 |
| HPMCSE polymer (S) | 0.5 |
| Chitosan polymer (C) | 0.15 |
| Calendula extract | 0.2 |
| Alcohol denatured | 10 |
| 1,3 propanediol | 2 |
| Caprylil capril triglyceride | 2 |
| Ethyl hexyl glycerin | 1 |
| Decanediol | 0.5 |
| Bisabolol | 0.1 |
| Pomegranate oil | 0.5 |
| Rosemary oil | 0.1 |
| Thymol | 0.1 |
| Menthol | 0.1 |
| Orange oil | 0.2 |
| Vetiver oil | 0.02 |
| Resveratrol | 0.5 |
| Red sandalwood extract | 0.1 |
| Chlorhexidine gluconate | 0.05 |

8

Formulation Sample SE-1

| Ingredient | % (w/w) |
| --- | --- |
| Salicylic acid | 2 |
| Base ingredient | |
| Deionized Water | Q.S. to 100 |
| Zinc gluconate | 0.2 |
| Zinc lactate | 0.2 |
| Aloe powder | 0.2 |
| Glycolic acid | 0.5 |
| Lactic acid | 0.2 |
| BTMSCB emulsifier (E) | 2.5 |
| Polawax ™ emulsifier (E) | 3 |
| HPMCSE polymer (S) | 0.5 |
| Calendula extract | 0.2 |
| Alcohol denatured | 10 |
| 1,3 propanediol | 2 |
| Caprylil capril triglyceride | 2 |
| Ethyl hexyl glycerin | 1 |
| Decanediol | 0.5 |
| Bisabolol | 0.1 |
| Pomegranate oil | 0.5 |
| Rosemary oil | 0.1 |
| Thymol | 0.1 |
| Menthol | 0.1 |
| Orange oil | 0.2 |
| Vetiver oil | 0.02 |
| Resveratrol | 0.5 |
| Red sandalwood extract | 0.1 |
| Chlorhexidine gluconate | 0.05 |

Formulation Sample SE-2

| Ingredient | % (w/w) |
| --- | --- |
| Salicylic acid | 2 |
| Base ingredient | |
| Deionized Water | Q.S. to 100 |
| Zinc gluconate | 0.2 |
| Zinc lactate | 0.2 |
| Aloe powder | 0.2 |
| Glycolic acid | 0.5 |
| Lactic acid | 0.2 |
| BTMSCB emulsifier (E) | 2.5 |
| Polawax ™ emulsifier (E) | 3 |
| HPMCSE polymer (S) | 0.7 |
| Calendula extract | 0.2 |
| Alcohol denatured | 10 |
| 1,3 propanediol | 2 |
| Caprylil capril triglyceride | 2 |
| Ethyl hexyl glycerin | 1 |
| Decanediol | 0.5 |
| Bisabolol | 0.1 |
| Pomegranate oil | 0.5 |
| Rosemary oil | 0.1 |
| Thymol | 0.1 |
| Menthol | 0.1 |
| Orange oil | 0.2 |
| Vetiver oil | 0.02 |
| Resveratrol | 0.5 |
| Red sandalwood extract | 0.1 |
| Chlorhexidine gluconate | 0.05 |

Formulation Sample SCE-1

| Ingredient | % (w/w) |
| --- | --- |
| Salicylic acid | 2 |
| Base ingredient | |
| Deionized Water | Q.S. to 100 |
| Zinc gluconate | 0.2 |
| Zinc lactate | 0.2 |
| Aloe powder | 0.2 |
| Glycolic acid | 0.5 |
| Lactic acid | 0.2 |
| BTMSCB emulsifier (E) | 1.5 |
| Polawax ™ emulsifier (E) | 1.5 |
| HPMCSE polymer (S) | 0.55 |
| Chitosan (C) | 0.3 |
| Calendula extract | 0.2 |
| Alcohol denatured | 10 |
| 1,3 propanediol | 2 |
| Caprylil capril triglyceride | 2 |
| Ethyl hexyl glycerin | 1 |
| Decanediol | 0.5 |
| Bisabolol | 0.1 |
| Pomegranate oil | 0.5 |
| Rosemary oil | 0.1 |
| Thymol | 0.1 |
| Menthol | 0.1 |
| Orange oil | 0.2 |
| Vetiver oil | 0.02 |
| Resveratrol | 0.5 |
| Red sandalwood extract | 0.1 |
| Chlorhexidine gluconate | 0.05 |

Formulation Sample SCE-2

| Ingredient | % (w/w) |
| --- | --- |
| Salicylic acid | 2 |
| Base ingredient | |
| Deionized Water | Q.S. to 100 |
| Zinc gluconate | 0.2 |
| Zinc lactate | 0.2 |
| Aloe powder | 0.2 |
| Glycolic acid | 0.5 |
| Lactic acid | 0.2 |
| BTMSCB emulsifier (E) | 2.5 |
| Polawax ™ emulsifier (E) | 3 |
| HPMCSE polymer (S) | 0.5 |
| Chitosan (C) | 0.15 |
| Calendula extract | 0.2 |
| Alcohol denatured | 10 |
| 1,3 propanediol | 2 |
| Caprylil capril triglyceride | 2 |
| Ethyl hexyl glycerin | 1 |
| Decanediol | 0.5 |
| Bisabolol | 0.1 |
| Pomegranate oil | 0.5 |
| Rosemary oil | 0.1 |
| Thymol | 0.1 |
| Menthol | 0.1 |
| Orange oil | 0.2 |
| Vetiver oil | 0.02 |
| Resveratrol | 0.5 |
| Red sandalwood extract | 0.1 |
| Chlorhexidine gluconate | 0.05 |

Stability of the Formulations (EC, SC, SE-1, SE-2, SCE-1 and SCE-2) at 7 days is 40° C. is shown in the FIGURE.

Conclusion: As can be seen from the above FIGURE, only formulations containing HPMCSE polymer(S), emulsifiers and Chitosan (SCE) resulted in a uniform gel. SE-2 formulation where S is 0.7% and emulsifier (5.5%) was also resulted in a uniform gel.

However, SE-which is S (0.5% and emulsifiers (5.5%), EC which is emulsifier and Chitosan, SC which S and Chitosan were separated and did not form a uniform gel.

Various SCE formulations where concentrations of S ranging from 0.1 to 1% w/w, C ranging from 0.1 to 0.5% w/w, and E ranging from 0.4 to 5% w/w were also prepared and found to be stable.

Example 2

Antibacterial Efficacy of Combination of Salicylic Acid and Botanicals

Various botanicals, salicylic acid and combinations were mixed in FGZ gel and antibacterial efficacy was evaluated. Results are shown in the Tables below.

Table 1: Antibacterial Activity of Salicylic Acid and Botanicals in FGZ Base (Zone of Inhibition Test)

TABLE 1

| Ingredients in FGZ Base | Zone of inhibition (mm) |
| --- | --- |
| FGZ base (control) | 0 |
| Salicylic acid 2% | 1 |
| Botanical blend | 2 |
| Botanical blend + salicylic acid | 7.5 |

"Botanical blend" contains: pomegranate extract (0.5%), rosemary oil (0.1%), orange oil (0.2%), vetiver oil (0.02%), red sandal wood extract (0.1%), plant based benzyl alcohol (1%), plant based 1,3 propanediol (2%).

Conclusion: Botanical blend synergistically enhances the efficacy of salicylic acid.

Table 2: Antibacterial Activity (Rapidity of Kill Test Organism *S. aureus*)

Rapid kill (15 seconds) test tube method described in ASTM-E2783-1198751-1 (suspension test).

In vitro rapid-kill test was carried out according to ASTM E2783-11; 108 CFU mL$^{-1}$ microbial cultures were prepared in a TSA media in order to determine the antimicrobial activity of acne formulations. 0.9 mL acne formulation was kept in contact with 0.1 mL microbial cultures for 15 seconds and subsequently neutralized using agent DE. PBS was used as a control. In this study, an the acne product is considered effective if the log 10 reduction exhibits 3.0 or higher.

TABLE 2

| Ingredient in FGZ gel | Log reductrion from control growth |
| --- | --- |
| FGZ base (control) | 0 |
| Salicylic acid 2% | 2.1 |
| Botanical blend 1 | 1.2 |
| Botanical blend 2 | 1.2 |
| 0.05% chlorhexidine gluconate (preservative) | 0.2 |
| Botanical blend 1 + Salicylic acid | 3.8 |
| Botanical blend 2 + Salicylic acid | 3.8 |
| Botanical blend 1 + Salicylic acid + 0.05% Chlorhexidine | 4 |

Botanical Blend 1 contains: Rosemary oil (0.1%), Orange oil (0.2%), Vetiver oil (0.02%), Red sandalwood extract (0.1%), Benzyl alcohol (1%), Plant based 1,3 propanediol (2%).

Botanical Blend 2 contains: Pomegranate Extract (0.5%), Rosemary oil (0.1%), Orange oil (0.2%), Vetiver oil (0.02%), Red sandalwood extract (0.1%), Benzyl alcohol (1%), Plant based 1,3 propanediol (2%).

Conclusion: Botanical blends in combination with Salicylic acid show higher antibacterial efficacy.

Example 3

Various SCE-Zinc salts film (FGZ) formulation containing salicylic acid and botanicals (FGZB) e.g. cleanser, lotion and spot cream were prepared as below and were found to be stable and effective.

HGZB Cleanser C-7

| Ingredient | % w/w |
|---|---|
| Phase A (50-60) | |
| Water | 47.3 |
| Zinc lactate | 0.2 |
| Zinc gluconate | 0.2 |
| Methocel | 1 |
| Polyquaternium 10 | 0.5 |
| Pluronic ® F-87 | 1.5 |
| BTMSCB | 0.2 |
| Polawax ™ | 0.2 |
| Cocoamido propyl betaine | 9 |
| Glycolic acid | 0.5 |
| Lactic Acid | 0.2 |
| Sodium chloride | 0.2 |
| Sangelose ® 90 L (1%) | 10 |
| Chitosan (3%) | 4 |
| Aloe 1X | 3 |
| Calendula Extract | 1 |
| | |
| Total Phase A | 79 |
| Phase B Botanical Blend | |
| | |
| SDA 40B | 15 |
| Benzyl alcohol | 1 |
| Red Sandalwood | 0.09 |
| Salicylic acid | 1 |
| C3 curcumin | 0.01 |
| Octanediol | 0.5 |
| Ethylhexyl Glycerin | 1 |
| Phenoxy ethanol | 0.7 |
| Farnasol | 0.3 |
| Thymol | 0.1 |
| Menthol | 0.1 |
| CHG (20%) | 1 |
| Orange oil | 0.2 |
| | |
| Total Phase B | 21 |

HGZB Cleanser C-8

| Ingredient | % w/w |
|---|---|
| Phase A (50-60) | |
| Water | 46.7 |
| Zinc lactate | 0.2 |
| Zinc gluconate | 0.2 |
| Methocel | 1 |
| Polyquaternium 10 | 0.5 |
| Pluronic ® F-87 | 1.5 |
| BTMSCB | 0.5 |
| Polawax ™ | 0.5 |
| Jojoba oil | 2 |
| Cocoamido propyl betaine | 9 |
| Glycolic acid | 0.5 |
| Lactic Acid | 0.2 |
| Sodium chloride | 0.2 |
| Sangelose ® 90 L(1%) | 10 |

HGZB Cleanser C-8

| Ingredient | % w/w |
|---|---|
| Chitosan (3%) | 4 |
| Aloe 1X | 3 |
| Calendula Extract | 1 |
| | |
| Total Phase A | 79 |
| Phase B Botanical Blend | |
| | |
| SDA 40B | 15 |
| Benzyl alcohol | 1 |
| Red Sandalwood | 0.09 |
| Salicylic acid | 1 |
| C3 curcumin | 0.01 |
| Octanediol | 0.5 |
| Ethylhexyl Glycerin | 1 |
| Phenoxy ethanol | 0.7 |
| Farnasol | 0.3 |
| Thymol | 0.1 |
| Menthol | 0.1 |
| CHG (20%) | 1 |
| Orange oil | 0.2 |
| | |
| Total Phase B | 21 |

HGZB Cleanser F-3 pH 4.5

| Ingredient | % w/w |
|---|---|
| Phase A (50-60) | |
| Water | 57.8 |
| Zinc lactate | 0.2 |
| Zinc gluconate | 0.1 |
| Panthenol | 0.5 |
| Pluronic ® F-87 | 1.5 |
| BTMSCB | 0.1 |
| Polawax ™ | 0.1 |
| Cocoamido propyl betaine | 11 |
| Glycolic acid | 0.5 |
| Lactic Acid | 0.2 |
| | |
| Total Phase A | 72 |
| Phase B Botanical Blend | |
| | |
| Zemea ® propanediol | 3 |
| SDA 40B denatured alcohol | 10 |
| Benzyl alcohol | 1 |
| Salicylic acid | 1 |
| Decanediol | 0.5 |
| Ethylhexyl Glycerin | 1 |
| Phenoxy ethanol | 0.7 |
| Aloe Vera 1X | 2 |
| Farnasol | 0.3 |
| CHG (20%) | 1 |
| Orange oil | 0.5 |
| Incromine ® Oxide | 2 |
| Sangelose ® 60L (1% in 1:1 mix of SDA-40 & Water) | 5 |
| | |
| Total Phase B | 28 |
| | |
| | 100 |

HGZB Cleanser F-4 pH 4 5

| Ingredient | % w/w |
|---|---|
| Phase A (50-60) | |
| Water | 59.3 |
| Zinc lactate | 0.2 |
| Zinc gluconate | 0.1 |
| Panthenol | 0.5 |
| Pluronic ® F-87 | 2 |
| BTMSCB | 0.1 |
| Polawax ™ | 0.1 |
| Cocoamido propyl betaine | 11 |
| Glycolic acid | 0.5 |
| Lactic Acid | 0.2 |
| Total Phase A | 74 |
| Phase B Botanical Blend | |
| Zemea ® propanediol | 3 |
| SDA 40B | 10 |
| Benzyl alcohol | 1 |
| Salicylic acid | 1 |
| Decanediol | 0.5 |
| Ethylhexyl Glycerin | 1 |
| Phenoxy ethanol | 0.7 |
| Aloe Vera 1X | 2 |
| Farnasol | 0.3 |
| CHG (20%) | 1 |
| Orange oil | 0.5 |
| Sangelose ® 60L (1% in 1:1 mix of SDA-40 & Water) | 5 |
| Total Phase B | 26 |

HGZB Cleanser F-5 pH 4.5

| Ingredient | % w/w |
|---|---|
| Phase A (50-60) | |
| Water | 58.75 |
| Zinc lactate | 0.2 |
| Zinc gluconate | 0.1 |
| Panthenol | 0.5 |
| Pluronic ® F-87 | 2 |
| BTMSCB | 0.1 |
| Polawax ™ | 0.1 |
| Cocoamido propyl betaine | 11 |
| Glycolic acid | 0.5 |
| Lactic Acid | 0.2 |
| Total Phase A | 73.45 |
| Phase B Botanical Blend | |
| Zemea ® propanediol | 3 |
| SDA 40B | 10 |
| Benzyl alcohol | 1 |
| Salicylic acid | 1 |
| Decanediol | 0.5 |
| Ethylhexyl Glycerin | 1 |
| Phenoxy ethanol | 0.7 |
| Aloe Vera 1X | 2 |
| Farnasol | 0.3 |
| Lemon extract | 0.5 |
| Thymol | 0.05 |
| CHG (20%) | 1 |
| Orange oil | 0.5 |
| Sangelose ® 60L (1% in 1:1 mix of SDA-40 & Water) | 5 |
| Total Phase B | 26.55 |
| | 100 |

HGZB Cleanser F-7 pH 4.0

| Ingredient | % w/w |
|---|---|
| Phase A (50-60) | |
| Water | 49.95 |
| Sodium Chloride | 0.4 |
| Hydroxyethylcellulose | 0.2 |
| Zinc lactate | 0.2 |
| Zinc gluconate | 0.1 |
| Panthenol | 0.5 |
| Pluronic ® F-87 | 2.5 |
| BTMSCB | 0.1 |
| Polawax ™ | 0.1 |
| Cocoamido propyl betaine | 15 |
| Glycolic acid | 1 |
| Lactic Acid | 0.2 |
| Sangelose ® 60L (1%) | 5 |
| Total Phase A | 75.25 |
| Orange Flavor | 1 |
| Phase B Botanical Blend | |
| Zemea ® propanediol | 3. |
| SDA 40B | 10 |
| Benzyl alcohol | 1 |
| Salicylic acid | 1 |
| Decanediol | 0.5 |
| Ethylhexyl Glycerin | 1 |
| Phenoxy ethanol | 0.7 |
| Aloe Vera 1X | 2 |
| Farnasol | 0.3 |
| Lemon extract | 0.5 |
| Thymol | 0.05 |
| CHG (20%) | 1 |
| White tea extract | 0.5 |
| Resveratrol extract | 0.5 |
| Vitamin E | 0.1 |
| Vitamin C | 0.1 |
| Orange oil | 0.5 |
| Tween ® 20 | 1 |
| Total Phase B | 23.75 |
| | 100 |

HGZB Cleanser F-8 pH 4.0

| Ingredient | % w/w |
|---|---|
| Phase A (50-60) | |
| Water | 49.81 |
| Sodium Chloride | 0.4 |
| Ucare ® polyquaternium-10 emulsifier | 0.5 |
| Zinc lactate | 0.2 |
| Zinc gluconate | 0.1 |
| Panthenol | 0.5 |
| Pluronic ® F-87 | 2.5 |
| BTMSCB | 0.1 |
| Polawax ™ | 0.1 |
| Cocoamido propyl betaine | 15 |
| Glycolic acid | 1 |
| Lactic Acid | 0.2 |
| Sangelose ® 60L (1%) | 5 |
| Total Phase A | 75.41 |
| Orange Flavor | 1 |
| Phase B Botanical Blend | |
| Zemea ® propanediol | 3 |
| SDA 40B | 10 |

15

-continued

HGZB Cleanser F-8
pH 4.0

| Ingredient | % w/w |
|---|---|
| Benzyl alcohol | 1 |
| Salicylic acid | 1 |
| Decanediol | 0.5 |
| Ethylhexyl Glycerin | 1 |
| Phenoxy ethanol | 0.7 |
| Aloe Vera 1X | 2 |
| Farnasol | 0.3 |
| Lemon extract | 0.5 |
| Thymol | 0.05 |
| CHG (20%) | 1 |
| White tea extract | 0.5 |
| Resveratrol extract | 0.5 |
| Vitamin E | 0.02 |
| Vitamin C | 0.02 |
| Orange oil | 0.5 |
| Tween ® 20 | 1 |
| Total Phase B | 23.59 |
| | 100 |

HGZB Cleanser F-9
pH 4.0

| Ingredient | % w/w |
|---|---|
| Phase A (50-60) | |
| Water | 40.55 |
| Sodium Chloride | 0.4 |
| Zinc lactate | 0.2 |
| Zinc gluconate | 0.1 |
| Panthenol | 0.5 |
| Pluronic ® F-87 | 3 |
| BTMSCB | 0.1 |
| Polawax ™ | 0.1 |
| Cocoamido propyl betaine | 15 |
| Glycolic acid | 1 |
| Lactic Acid | 0.2 |
| Sangelose ® 60L (1%) | 10 |
| Total Phase A | 71.15 |
| Orange Flavor | 0.5 |
| Phase B Botanical Blend | |
| Zemea ® propanediol | 3 |
| SDA 40B | 15 |
| Benzyl alcohol | 1 |
| Salicylic acid | 1 |
| Decanediol | 0.5 |
| Ethylhexyl Glycerin | 1 |
| Phenoxy ethanol | 0.7 |
| Aloe Vera 1X | 2 |
| Farnasol | 0.3 |
| Lemon extract | 0.5 |
| Orange oil | 0.3 |
| Thymol | 0.05 |
| CHG (20%) | 1 |
| White tea extract | 0.5 |
| Resveratrol extract | 0.5 |
| Tween ® 20 | 1 |
| Total Phase B | 28.35 |
| | 100 |

16

HGZB Cleanser F-13
pH 4.0

| Ingredient | % w/w |
|---|---|
| Phase A (50-60) | |
| Water | 36.95 |
| Zinc lactate | 0.2 |
| Zinc gluconate | 0.1 |
| Panthenol | 0.5 |
| Pluronic ® F-87 | 3 |
| BTMSCB | 0.2 |
| Polawax ™ | 0.2 |
| Cocoamido propyl betaine | 15 |
| Glycolic acid | 1 |
| Lactic Acid | 0.2 |
| Total Phase A | 57.35 |
| Orange Flavor | 0.5 |
| NaOH (10N) | 1.3 |
| Phase B Botanical Blend | |
| Zemea ® propanediol | 3 |
| Benzyl alcohol | 1 |
| Salicylic acid | 1 |
| Ethylhexyl Glycerin | 1 |
| Phenoxy ethanol | 0.7 |
| Aloe Vera 1X | 2 |
| Farnasol | 0.3 |
| Lemon extract | 0.5 |
| Thymol | 0.05 |
| CHG (20%) | 1 |
| Green tea extract | 1 |
| Orange oil | 0.3 |
| Tween ® 20 | 1 |
| SDA 40B | 18 |
| Sangelose ® 90L (1%) | 10 |
| Total Phase B | 40.85 |
| | 100 |

HGZB Cleanser F-14 pH 4.0

| Ingredient | % w/w |
|---|---|
| Phase A (65-70) | |
| Water | 36.22 |
| Zinc lactate | 0.4 |
| Zinc gluconate | 0.2 |
| Panthenol | 0.5 |
| Pluronic ® F-87 | 3 |
| Glycolic acid (70% Solution) | 1.43 |
| Lactic Acid | 0.2 |
| BTMSCB | 0.2 |
| Polawax ™ | 0.2 |
| Sangelose ® 90L (1%) | 10 |
| Cocoamido propyl betaine | 15 |
| Total Phase A | 67.35 |
| Orange Fragrance #180494 | 0.5 |
| NaOH(10N) | 1.3 |
| Phase B Botanical Blend | |
| SDA 40B | 18 |
| Zemea ® propanediol | 3 |
| Thymol | 0.05 |
| Benzyl alcohol | 1 |
| Ethylhexyl Glycerin | 1 |
| Phenoxy ethanol | 0.7 |
| Salicylic acid | 1 |
| Aloe Vera 1X | 2 |
| Farnasol | 0.3 |
| Lemon extract | 0.5 |
| CHG (20%) | 1 |

-continued

HGZB Cleanser F-14 pH 4.0

| Ingredient | % w/w |
|---|---|
| Green tea extract | 1 |
| Orange oil | 0.3 |
| Tween ® 20 | 1 |
| Total Phase B | 30.85 |
| | 100 |

HGZB Cleanser F-15 pH 4.0

| Ingredient | % w/w |
|---|---|
| Phase A (65-70) | |
| Water | 39.22 |
| Zinc lactate | 0.4 |
| Zinc gluconate | 0.2 |
| Panthenol | 0.5 |
| Glycolic acid (70% Solution) | 1.43 |
| Lactic Acid | 0.2 |
| BTMSCB | 0.2 |
| Polawax ™ | 0.2 |
| Sangelose ® 90L (1%) | 10 |
| Cocoamido propyl betaine | 15 |
| Total Phase A | 67.35 |
| Orange Fragrance #180494 | 0.5 |
| NaOH (10N) | 1.3 |
| Phase B Botanical Blend | |
| SDA 40B | 18 |
| Zemea ® propanediol | 3 |
| Thymol | 0.05 |
| Benzyl alcohol | 1 |
| Ethylhexyl Glycerin | 1 |
| Phenoxy ethanol | 0.7 |
| Salicylic acid | 1 |
| Aloe Vera 1X | 2 |
| Farnasol | 0.3 |
| Lemon extract | 0.5 |
| CHG (20%) | 1 |
| Green tea extract | 1 |
| Orange oil | 0.3 |
| Tween ® 20 | 1 |
| Total Phase B | 30.85 |
| | 100 |

HGZB Cleanser F-16 pH 4.0

| Ingredient | % w/w |
|---|---|
| Phase A (65-70) | |
| Water | 38.72 |
| Zinc lactate | 0.4 |
| Zinc gluconate | 0.2 |
| Panthenol | 0.5 |
| Glycolic acid (70% Solution) | 1.43 |
| Xanthan Gum | 0.5 |
| Lactic Acid | 0.2 |
| BTMSCB | 0.2 |

-continued

HGZB Cleanser F-16 pH 4.0

| Ingredient | % w/w |
|---|---|
| Polawax ™ | 0.2 |
| Sangelose ® 90L (1%) | 10 |
| Cocoamido propyl betaine | 15 |
| Total Phase A | 67.35 |
| Orange Fragrance #180494 | 0.5 |
| NaOH (10N) | 1.3 |
| Phase B Botanical Blend | |
| SDA 40B | 18 |
| Zemea ® propanediol | 3 |
| Thymol | 0.05 |
| Benzyl alcohol | 1 |
| Ethylhexyl Glycerin | 1 |
| Phenoxy ethanol | 0.7 |
| Salicylic acid | 1 |
| Aloe Vera 1X | 2 |
| Farnasol | 0.3 |
| Lemon extract | 0.5 |
| CHG (20%) | 1 |
| Green tea extract | 1 |
| Orange oil | 0.3 |
| Tween ® 20 | 1 |
| Total Phase B | 30.85 |
| | 100 |

FGZB Lotion G-1

| Ingredient | % w/w |
|---|---|
| Phase A (50-60) | |
| Water | 17.63 |
| Zinc lactate | 0.2 |
| Zinc gluconate | 0.2 |
| D-L panthenol | 0.5 |
| Lactic acid | 0.2 |
| Glycolic acid | 0.5 |
| Aloe 100X | 1 |
| BTMSCB | 1.5 |
| Polawax ™ NF | 1.5 |
| Jojoba oil (Viva) | 2 |
| Chitosan 3% | 8 |
| Calendula extract (100%/oil) | 0.2 |
| Cool to 30-40° C. | |
| Phase B | |
| Sangelose ® 90 L 1% | 50 |
| Add Phase B to Phase A | |
| Total Phase A + B | 83.7 |
| Phase C Botanical Blend | |
| Zemea ® propanediol | 7 |
| Ethyl Hexyl Glycerin | 1 |
| butylene glycol | 2 |
| salicylic acid | 2 |
| Bisabolol | 0.1 |
| Phenoxyethanol | 0.7 |
| Pomegranate oil | 0.3 |
| Rosemary oil | 0.1 |
| orange oil | 0.2 |
| Vetiver oil | 0.02 |

-continued

FGZB Lotion G-1

| Ingredient | % w/w |
|---|---|
| Sorbitan monolaurate | 0.5 |
| CHG (20%) | 0.25 |
| Vitamin E | 0.2 |
| Vitamin C | 0.1 |
| silicone Shinetsu KF6038 | 1 |
| Red sandalwood extract | 0.1 |
| Resveratrol BT | 0.5 |
| white tea extract | 0.5 |
| | |
| Total Phase C | 16.57 |

FGZB Lotion G-3

| Ingredient | % w/w |
|---|---|
| Phase A (50-60) | |
| | |
| Water | 19.03 |
| Zinc lactate | 0.2 |
| Zinc gluconate | 0.2 |
| Lactic acid | 0.2 |
| Glycolic acid | 0.5 |
| Aloe 100X | 0.2 |
| BTMSCB | 1 |
| Polawax ™ NF | 1 |
| Cool to 30-40° C. | |
| Phase B | |
| | |
| Sangelose ® 90 L 1% | 52 |
| Add Phase B to Phase A | |
| Chitosan 3% | 10 |
| Calendula extract (100%/oil) | 1 |
| | |
| Total Phase A + B | 85.33 |
| Phase C Botanical Blend | |
| | |
| Zemea ® propanediol | 5 |
| Ethyl Hexyl Glycerin | 1 |
| butylene glycol | 3 |
| Benzyl alcohol | 0.5 |
| salicylic acid | 2 |
| Bisabolol | 0.1 |
| Decanediol | 0.5 |
| Farnesol | 0.3 |
| Pomegranate oil | 0.5 |
| Rosemary oil | 0.1 |
| Orange oil | 0.1 |
| Vetiver oil | 0.02 |
| CHG (20%) | 0.25 |
| Vitamin E | 0.2 |
| Red sandalwood extract | 0.1 |
| Resveratrol BT | 0.5 |
| White tea extract | 0.5 |
| | |
| Total Phase C | 14.67 |

FGZB Lotion G-3A

| Ingredient | % w/w |
|---|---|
| Phase A (50-60) | |
| | |
| Water | 17.03 |
| Zinc lactate | 0.2 |
| Zinc gluconate | 0.2 |
| Lactic acid | 0.2 |
| Glycolic acid | 0.5 |
| Aloe 100X | 0.2 |
| BTMSCB | 1.0 |

-continued

FGZB Lotion G-3A

| Ingredient | % w/w |
|---|---|
| Polawax ™ NF | 1.0 |
| Cupuacu Butter | 2.0 |
| Cool to 30-40° C. | |
| Phase B | |
| | |
| Sangelose ® 90 L 1% | 52 |
| Add Phase B to Phase A | |
| Chitosan 3% | 10 |
| Calendula extract (100%/oil) | 1 |
| | |
| Total Phase A + B | 85.33 |
| Phase C Botanical Blend | |
| | |
| Zemea ® propanediol | 5 |
| Ethyl Hexyl Glycerin | 1 |
| butylene glycol | 3 |
| Benzyl alcohol | 0.5 |
| salicylic acid | 2 |
| Bisabolol | 0.1 |
| Decanediol | 0.5 |
| Farnesol | 0.3 |
| Pomegranate oil | 0.5 |
| Rosemary oil | 0.1 |
| Orange oil | 0.1 |
| Vetiver oil | 0.02 |
| CHG (20%) | 0.25 |
| Vitamin E | 0.2 |
| Red sandalwood extract | 0.1 |
| Resveratrol BT | 0.5 |
| White tea extract | 0.5 |
| | |
| Total Phase C | 14.67 |

FGZB Lotion G-3B

| Ingredient | % w/w |
|---|---|
| Phase A (50-60) | |
| | |
| Water | 18.03 |
| Zinc lactate | 0.2 |
| Zinc gluconate | 0.2 |
| Lactic acid | 0.2 |
| Glycolic acid | 0.5 |
| Aloe 100X | 0.2 |
| BTMSCB | 1.5 |
| Polawax ™ NF | 1.5 |
| Cool to 30-40° C. | |
| Phase B | |
| | |
| Sangelose ® 90 L 1% | 52 |
| Add Phase B to Phase A | |
| Chitosan 3% | 10 |
| Calendula extract (100%/oil) | 1 |
| | |
| Total Phase A + B | 85.33 |
| Phase C Botanical Blend | |
| | |
| Zemea ® propanediol | 5 |
| Ethyl Hexyl Glycerin | 1 |
| butylene glycol | 3 |
| Benzyl alcohol | 0.5 |
| salicylic acid | 2 |
| Bisabolol | 0.1 |
| Decanediol | 0.5 |
| Farnesol | 0.3 |
| Pomegranate oil | 0.5 |
| Rosemary oil | 0.1 |
| Orange oil | 0.1 |
| Vetiver oil | 0.02 |
| CHG (20%) | 0.25 |
| Vitamin E | 0.2 |

21

-continued

FGZB Lotion G-3B

| Ingredient | % w/w |
|---|---|
| Red sandalwood extract | 0.1 |
| Resveratrol BT | 0.5 |
| White tea extract | 0.5 |
| Total Phase C | 14.67 |

FGZB Lotion G-3C

| Ingredient | % w/w |
|---|---|
| Phase A (50-60) | |
| Water | 18.03 |
| Zinc lactate | 0.2 |
| Zinc gluconate | 0.2 |
| Lactic acid | 0.2 |
| Glycolic acid | 0.5 |
| Aloe 100X | 0.2 |
| BTMSCB | 1 |
| Polawax ™ NF | 1 |
| Cool to 30-40° C. | |
| Phase B | |
| Sangelose ® 90 L 1% | 52 |
| Add Phase B to Phase A | |
| Chitosan 3% | 10 |
| Calendula extract (100%/oil) | 1 |
| Total Phase A + B | 84.24 |
| Phase C Botanical Blend | |
| Zemea ® propanediol | 5 |
| Ethyl Hexyl Glycerin | 1 |
| butylene glycol | 3 |
| Benzyl alcohol | 0.5 |
| salicylic acid | 2 |
| Bisabolol | 0.1 |
| Decanediol | 0.5 |
| Farnesol | 0.3 |
| Pomegranate oil | 0.5 |
| Rosemary oil | 0.1 |
| Orange oil | 0.1 |
| Vetiver oil | 0.02 |
| CHG (20%) | 0.25 |
| Vitamin E | 0.2 |
| Red sandalwood extract | 0.1 |
| Resveratrol BT | 0.5 |
| White tea extract | 0.5 |
| Silicone KF 6038 | 1.0 |
| Total Phase C | 15.67 |

FGZB Lotion G-4

| Ingredient | % w/w |
|---|---|
| Phase A (50-60) | |
| Water | 15.03 |
| Zinc lactate | 0.2 |
| Zinc gluconate | 0.2 |
| Lactic acid | 0.2 |
| Glycolic acid | 0.5 |
| Aloe 100X | 0.2 |
| BTMSCB | 1.5 |

22

-continued

FGZB Lotion G-4

| Ingredient | % w/w |
|---|---|
| Polawax ™ NF | 1.5 |
| Cupuacu Butter | 2 |
| Cool to 30-40° C. | |
| Phase B | |
| Sangelose ® 90 L 1% | 52 |
| Add Phase B to Phase A | |
| Chitosan 3% | 10 |
| Calendula extract (100%/oil) | 1 |
| Total Phase A + B | 84.33 |
| Phase C Botanical Blend | |
| Zemea ® propanediol | 5 |
| Ethyl Hexyl Glycerin | 1 |
| butylene glycol | 3 |
| Benzyl alcohol | 0.5 |
| salicylic acid | 2 |
| Bisabolol | 0.1 |
| Decanediol | 0.5 |
| Farnesol | 0.3 |
| Pomegranate oil | 0.5 |
| Rosemary oil | 0.1 |
| Orange oil | 0.1 |
| Vetiver oil | 0.02 |
| CHG (20%) | 0.25 |
| Vitamin E | 0.2 |
| Red sandalwood extract | 0.1 |
| Resveratrol BT | 0.5 |
| White tea extract | 0.5 |
| Silicone KF6038 | 1 |
| Total Phase C | 15.67 |

FGZB Lotion G-5A

| Ingredient | % w/w |
|---|---|
| Phase A (50-60) | |
| Water | 15.69 |
| Zinc lactate | 0.2 |
| Zinc gluconate | 0.2 |
| Lactic acid | 0.2 |
| Glycolic acid | 0.5 |
| Aloe 100X | 0.2 |
| BTMSCB | 1.5 |
| Polawax ™ NF | 1.5 |
| Cupuacu Butter | 2 |
| Phase B | |
| Sangelose ® 90 L 1% | 52 |
| Chitosan 3% | 10 |
| Calendula extract (100%/oil) | 1 |
| Total Phase A + B | 84.99 |
| Phase C Botanical Blend | |
| Zemea ® propanediol | 5 |
| Ethyl Hexyl Glycerin | 1 |
| butylene glycol | 3 |
| Benzyl alcohol | 0.5 |
| Salicylic acid | 2 |
| Bisabolol | 0.1 |
| Decanediol | 0.5 |
| Farnesol | 0.3 |
| Pomegranate oil | 0.5 |
| Rosemary oil | 0.1 |
| Orange oil | 0.5 |
| Vetiver oil | 0.01 |
| CHG (20%) | 0.25 |
| Vitamin E | 0.1 |

-continued

FGZB Lotion G-5A

| Ingredient | % w/w |
|---|---|
| Vitamin C | 0.1 |
| Red sandalwood extract (10%) | 0.05 |
| Resveratrol BT | 0.5 |
| White Tea Ext BT | 0.5 |
| Total Phase C | 15.01 |
| | 100 |

FGZB Lotion G-6

| Ingredient | % w/w |
|---|---|
| Phase A (50-60) | |
| Water | 14.2 |
| Zinc lactate | 0.2 |
| Zinc gluconate | 0.2 |
| Panthenol | 0.5 |
| Lactic acid | 0.2 |
| Glycolic acid | 0.5 |
| Aloe 100X | 0.2 |
| BTMSCB | 1.5 |
| Polawax ™ NF | 1.5 |
| Cupuacu Butter | 2 |
| Phase B | |
| Sangelose ® 90 L 1% | 52 |
| Chitosan 5% | 10 |
| Calendula extract (100%/oil) | 1 |
| Total Phase A + B | 84 |
| Orange Cream Flavor | 1 |
| Phase C Botanical Blend | |
| Zemea ® propanediol | 4.5 |
| Ethyl Hexyl Glycerin | 1 |
| butylene glycol | 3 |
| Benzyl alcohol | 0.5 |
| Salicylic acid | 2 |
| Bisabolol | 0.1 |
| Decanediol | 0.5 |
| Farnesol | 0.3 |
| Pomegranate Extract | 0.5 |
| Lemon extract | 0.5 |
| Thymol | 0.05 |
| Rosemary oil | 0.1 |
| Orange oil | 0.3 |
| CHG (20%) | 0.25 |
| Vitamin E | 0.1 |
| Vitamin C | 0.1 |
| Resveratrol BT | 0.5 |
| Witch Hazel (5% Concentrate) | 0.2 |
| White Tea Ext BT | 0.5 |
| Total Phase C | 15 |
| | 100 |

FGZB Lotion G-7

| Ingredient | % w/w |
|---|---|
| Phase A (50-60) | |
| Water | 11.15 |
| Zinc lactate | 0.2 |
| Zinc gluconate | 0.2 |
| Panthenol | 0.5 |

-continued

FGZB Lotion G-7

| Ingredient | % w/w |
|---|---|
| Lactic acid | 0.2 |
| Glycolic acid | 0.5 |
| Aloe 100X | 0.2 |
| BTMSCB | 2 |
| Polawax ™ NF | 2 |
| Cupuacu Butter | 2 |
| Sangelose ® 90 L 1% | 52 |
| Chitosan 5% | 10 |
| Calendula extract (100%) | 1 |
| Total Phase A | 81.95 |
| Orange Cream Flavor | 1 |
| NaOH (10N) | 2.05 |
| Phase B Botanical Blend | |
| Zemea ® propanediol | 4.5 |
| Ethyl Hexyl Glycerin | 1 |
| butylene glycol | 3 |
| Benzyl alcohol | 0.5 |
| Salicylic acid | 2 |
| Bisabolol | 0.1 |
| Decanediol | 0.5 |
| Farnesol | 0.3 |
| Pomegranate Extract | 0.5 |
| Lemon extract | 0.5 |
| Thymol | 0.05 |
| Rosemary oil | 0.1 |
| Orange oil | 0.3 |
| CHG (20%) | 0.25 |
| Vitamin E | 0.1 |
| Vitamin C | 0.1 |
| Resveratrol BT | 0.5 |
| Witch Hazel (5% Concentrate) | 0.2 |
| White Tea Ext BT | 0.5 |
| Total Phase B | 15 |
| | 100 |

| Ingredient | % w/w |
|---|---|
| Phase A (50-60) | |
| Water | 10.8 |
| Zinc lactate | 0.2 |
| Zinc gluconate | 0.2 |
| Panthenol | 0.5 |
| Lactic acid | 0.2 |
| Glycolic acid | 0.5 |
| Aloe 100X | 0.2 |
| BTMSCB | 2 |
| Polawax ™ NF | 2 |
| Sangelose ® 90 L 1% | 52 |
| Chitosan 5% | 12 |
| Calendula extract (100%) | 0.5 |
| Total Phase A | 80.55 |
| Orange Cream Flavor | 0.25 |
| NaOH (10N) | 2.05 |
| Phase B Botanical Blend | |
| Zemea ® propanediol | 4.5 |
| Ethyl Hexyl Glycerin | 1 |
| butylene glycol | 3 |
| Benzyl alcohol | 0.5 |
| Salicylic acid | 2 |
| Bisabolol | 0.1 |
| Decanediol | 0.5 |
| Farnesol | 0.3 |
| Grapefruit seed Extract | 0.5 |
| Pomegranate Extract | 0.5 |
| Lemon extract | 0.5 |

-continued

| Ingredient | % w/w |
|---|---|
| Thymol | 0.05 |
| Rosemary oil | 0.1 |
| Orange oil | 0.3 |
| CHG (20%) | 0.25 |
| Licorice Extract | 0.5 |
| Cranberry seed oil | 0.5 |
| Vitamin C | 0.1 |
| Resveratrol BT | 0.5 |
| Witch Hazel (5%) | 0.4 |
| white tea extract | 0.5 |
| Total Phase B | 16.6 |
| | 100 |

| Ingredient | % w/w |
|---|---|
| Phase A (50-60) | |
| Water | 63.30 |
| Zinc lactate | 0.2 |
| Zinc gluconate | 0.2 |
| Panthenol | 0.5 |
| Lactic acid | 0.2 |
| Glycolic acid | 0.5 |
| Aloe 100X | 0.2 |
| Sangelose ® 90 L | 0.5 |
| BTMSCB | 2 |
| Polawax ™ NF | 2 |
| Chitosan 5% | 10 |
| Calendula extract (100%) | 1 |
| Total Phase A | 80.8 |
| Orange Cream Flavor | 0.25 |
| NaOH (10N) | 2.05 |
| Phase B Botanical Blend | |
| Zemea ® propanediol | 4.5 |
| Ethyl Hexyl Glycerin | 1 |
| butylene glycol | 3 |
| Benzyl alcohol | 0.5 |
| Salicylic acid | 2 |
| Bisabolol | 0.1 |
| Decanediol | 0.5 |
| Farnesol | 0.3 |
| Grapefruit seed Extract | 0.5 |
| Pomegranate Extract | 0.5 |
| Lemon extract | 0.5 |
| Thymol | 0.05 |
| Basil oil | 0.1 |
| Rosemary oil | 0.1 |
| Orange oil | 0.2 |
| CHG (20%) | 0.25 |
| Licorice Extract | 0.5 |
| Cranberry seed oil | 0.5 |
| Vitamin C | 0.1 |
| Resveratrol BT | 0.5 |
| Witch Hazel (5%) | 0.4 |
| Green Tea Ext | 1 |
| Total Phase B | 17.1 |
| | 100 |

| Ingredient | % w/w |
|---|---|
| Phase A (65-70) | |
| Water | 9.64 |
| Zinc lactate | 0.4 |
| Zinc gluconate | 0.4 |

-continued

| Ingredient | % w/w |
|---|---|
| Panthenol | 0.5 |
| Lactic acid | 0.2 |
| Glycolic acid (70% Solution) | 0.71 |
| BTMSCB | 0.5 |
| Polawax ™ NF | 0.5 |
| hydroxyethylcellulose | 1.5 |
| Sangelose ® 90 L (1%) | 50 |
| Stearyl Alcohol | 1 |
| Chitosan (3%) | 13 |
| Aloe 100X | 1 |
| Calendula extract (100%) | 0.5 |
| Total Phase A | 79.85 |
| Orange Cream Flavor #180491 | 1 |
| NaOH (10N) | 2.05 |
| Phase B Botanical Blend | |
| Zemea ® propanediol | 4 |
| Thymol | 0.05 |
| Ethyl Hexyl Glycerin | 1 |
| butylene glycol | 3 |
| Benzyl alcohol | 0.5 |
| Salicylic acid | 2 |
| Decanediol | 0.5 |
| Bisabolol | 0.1 |
| Farnesol | 0.3 |
| Grapefruit seed Extract | 0.5 |
| Pomegranate Extract | 0.5 |
| Lemon extract | 0.5 |
| Basil oil | 0.1 |
| Rosemary oil | 0.1 |
| Orange oil | 0.2 |
| CHG (20%) | 0.25 |
| Licorice Extract | 0.5 |
| Cranberry seed oil | 0.5 |
| Vitamin C | 0.1 |
| Resveratrol | 0.5 |
| Witch Hazel (5%) | 0.4 |
| Green Tea Ext | 1 |
| Frankincense oil | 0.5 |
| Total Phase B | 17.1 |
| | 100 |

| Ingredient | % w/w |
|---|---|
| Phase A (65-70) | |
| Water | 29.64 |
| Zinc lactate | 0.4 |
| Zinc gluconate | 0.4 |
| Panthenol | 0.5 |
| Lactic acid | 0.2 |
| Glycolic acid (70% Solution) | 0.71 |
| BTMSCB | 0.5 |
| Polawax ™ NF | 0.5 |
| hydroxyethylcellulose | 1.5 |
| Sangelose ® 90 L (1%) | 30 |
| Stearyl Alcohol | 1 |
| Chitosan (3%) | 13 |
| Aloe 100X | 1 |
| Calendula extract (100%) | 0.5 |
| Total Phase A | 79.85 |
| Orange Cream Flavor #180491 | 1 |
| NaOH (10N) | 2.05 |
| Phase B Botanical Blend | |
| Zemea ® propanediol | 4 |
| Thymol | 0.05 |
| Ethyl Hexyl Glycerin | 1 |
| butylene glycol | 3 |
| Benzyl alcohol | 0.5 |

-continued

| Ingredient | % w/w |
|---|---|
| Salicylic acid | 2 |
| Decanediol | 0.5 |
| Bisabolol | 0.1 |
| Farnesol | 0.3 |
| Grapefruit seed Extract | 0.5 |
| Pomegranate Extract | 0.5 |
| Lemon extract | 0.5 |
| Basil oil | 0.1 |
| Rosemary oil | 0.1 |
| Orange oil | 0.2 |
| CHG (20%) | 0.25 |
| Licorice Extract | 0.5 |
| Cranberry seed oil | 0.5 |
| Vitamin C | 0.1 |
| Resveratrol | 0.5 |
| Witch Hazel (5%) | 0.4 |
| Green Tea Ext | 1 |
| Frankincense oil | 0.5 |
| | |
| Total Phase B | 17.1 |
| | |
| | 100 |

| Ingredient | % w/w |
|---|---|
| Phase A (65-70) | |
| | |
| Water | 13.14 |
| Zinc lactate | 0.4 |
| Zinc gluconate | 0.4 |
| Panthenol | 0.5 |
| Lactic acid | 0.2 |
| Glycolic acid (70% Solution) | 0.71 |
| BTMSCB | 0.5 |
| Polawax ™ NF | 0.5 |
| Stearyl Alcohol | 1 |
| HEC | 1 |
| Sangelose ® 90 L (1%) | 50 |
| Chitosan (3%) | 10 |
| Aloe 100X | 1 |
| Calendula extract (100%) | 0.5 |
| | |
| Total Phase A | 79.85 |
| Orange Cream Flavor #180491 | 1 |
| NaOH (10N) | 2.05 |
| Phase B Botanical Blend | |
| | |
| Zemea ® propanediol | 4 |
| Thymol | 0.05 |
| Ethyl Hexyl Glycerin | 1 |
| butylene glycol | 3 |
| Benzyl alcohol | 0.5 |
| Salicylic acid | 2 |
| Decanediol | 0.5 |
| Bisabolol | 0.1 |
| Farnesol | 0.3 |
| Grapefruit seed Extract | 0.5 |
| Pomegranate Extract | 0.5 |
| Lemon extract | 0.5 |
| Basil oil | 0.1 |
| Rosemary oil | 0.1 |
| Orange oil | 0.2 |
| CHG (20%) | 0.25 |
| Licorice Extract | 0.5 |
| Cranberry seed oil | 0.5 |
| Vitamin C | 0.1 |

-continued

| Ingredient | % w/w |
|---|---|
| Resveratrol | 0.5 |
| Witch Hazel (5%) | 0.4 |
| Green Tea Ext | 1 |
| Frankincense oil | 0.5 |
| | |
| Total Phase B | 17.1 |
| | |
| | 100 |

| Ingredient | % w/w |
|---|---|
| Phase A (65-70) | |
| | |
| Water | 14.64 |
| Zinc lactate | 0.4 |
| Zinc gluconate | 0.4 |
| Panthenol | 0.5 |
| Lactic acid | 0.2 |
| Glycolic acid (70% Solution) | 0.71 |
| BTMSCB | 0.5 |
| Polawax ™ NF | 0.5 |
| Stearyl Alcohol | 1 |
| Sangelose ® 90 L (1%) | 50 |
| Chitosan (3%) | 10 |
| Aloe 100X | 1 |
| Calendula extract (100%) | 0.5 |
| | |
| Total Phase A | 80.35 |
| Orange Cream Flavor #180491 | 1 |
| NaOH (10N) | 2.05 |
| Phase B Botanical Blend | |
| | |
| Zemea ® propanediol | 4 |
| Thymol | 0.05 |
| Ethyl Hexyl Glycerin | 1 |
| butylene glycol | 3 |
| Benzyl alcohol | 0.5 |
| Salicylic acid | 2 |
| Decanediol | 0.5 |
| Bisabolol | 0.1 |
| Farnesol | 0.3 |
| Grapefruit seed Extract | 0.5 |
| Pomegranate Extract | 0.5 |
| Lemon extract | 0.5 |
| Basil oil | 0.1 |
| Rosemary oil | 0.1 |
| Orange oil | 0.2 |
| CHG (20%) | 0.25 |
| Licorice Extract | 0.5 |
| Vitamin C | 0.1 |
| Resveratrol | 0.5 |
| Witch Hazel (5%) | 0.4 |
| Green Tea Ext | 1 |
| Frankincense oil | 0.5 |
| | |
| Total Phase B | 16.6 |
| | |
| | 100 |

| Ingredient | % w/w |
|---|---|
| Water | 29.14 |
| Zinc lactate | 0.4 |
| Zinc gluconate | 0.4 |
| Panthenol | 0.5 |
| Lactic acid | 0.2 |
| Glycolic acid (70% Solution) | 0.71 |
| Incroquat ™ BTMS | 0.5 |
| Polawax ™ NF | 0.5 |
| hydroxyethylcellulose | 2 |
| Sangelose ® 90 L (1%) | 30 |

-continued

| Ingredient | % w/w |
|---|---|
| Stearyl Alcohol | 1 |
| Chitosan (3%) | 13 |
| Aloe 100X | 1 |
| Calendula extract (100%) | 0.5 |
| Total Phase A | 79.85 |
| Orange Cream Flavor #180491 | 1 |
| NaOH (10N) | 2.05 |
| Phase B Botanical Blend | |
| Zemea ® propanediol | 4 |
| Thymol | 0.05 |
| Ethyl Hexyl Glycerin | 1 |
| butylene glycol | 3 |
| Benzyl alcohol | 0.5 |
| Salicylic acid | 2 |
| Decanediol | 0.5 |
| Bisabolol | 0.1 |
| Farnesol | 0.3 |
| Grapefruit seed Extract | 0.5 |
| Pomegranate Extract | 0.5 |
| Lemon extract | 0.5 |
| Basil oil | 0.1 |
| Rosemary oil | 0.1 |
| Orange oil | 0.2 |
| CHG (20%) | 0.25 |
| Licorice Extract | 0.5 |
| Cranberry seed oil | 0.5 |
| Vitamin C | 0.1 |
| Resveratrol | 0.5 |
| Witch Hazel (5%) | 0.4 |
| Green Tea Ext | 1 |
| Frankincense oil | 0.5 |
| Total Phase B | 17.1 |
| | 100 |

| Ingredient | % w/w |
|---|---|
| Water | 28.64 |
| Zinc lactate | 0.4 |
| Zinc gluconate | 0.4 |
| Panthenol | 0.5 |
| Lactic acid | 0.2 |
| Glycolic acid (70% Solution) | 0.71 |
| Incroquat ™ BTMS | 0.5 |
| Polawax ™ NF | 0.5 |
| hydroxyethylcellulose | 2 |
| Sangelose ® 90 L (1%) | 30 |
| Stearyl Alcohol | 1 |
| Chitosan (3%) | 13 |
| Xanthan Gum | 0.5 |
| Aloe 100X | 1 |
| Calendula extract (100%) | 0.5 |
| Total Phase A | 79.85 |
| Orange Cream Flavor #180491 | 1 |
| NaOH (10N) | 2.05 |
| Phase B Botanical Blend | |
| Zemea ® propanediol | 4 |
| Thymol | 0.05 |
| Ethyl Hexyl Glycerin | 1 |
| butylene glycol | 3 |
| Benzyl alcohol | 0.5 |
| Salicylic acid | 2 |
| Decanediol | 0.5 |
| Bisabolol | 0.1 |
| Farnesol | 0.3 |
| Grapefruit seed Extract | 0.5 |
| Pomegranate Extract | 0.5 |
| Lemon extract | 0.5 |
| Basil oil | 0.1 |

-continued

| Ingredient | % w/w |
|---|---|
| Rosemary oil | 0.1 |
| Orange oil | 0.2 |
| CHG (20%) | 0.25 |
| Licorice Extract | 0.5 |
| Cranberry seed oil | 0.5 |
| Vitamin C | 0.1 |
| Resveratrol | 0.5 |
| Witch Hazel (5%) | 0.4 |
| Green Tea Ext | 1 |
| Frankincense oil | 0.5 |
| Total Phase B | 17.1 |
| | 100 |

| Ingredient | % w/w |
|---|---|
| Phase A (50-60) | |
| Water | 14 |
| Zinc lactate | 0.2 |
| Zinc gluconate | 0.2 |
| Aloe powder | 0.2 |
| Methocel ™ cellulose ether | 0.5 |
| EDTA | 0.1 |
| Panthenol | 0.5 |
| Lactic acid | 0.2 |
| Glycolic acid | 0.5 |
| BTMSCB | 2.5 |
| Polawax ™ NF | 3 |
| Sangelose ® 90 L Gel (1%) | 50 |
| Chitosan Gel (3%) | 5 |
| calendula ext(100%)/oil | 0.3 |
| Vitamin E | 0.2 |
| Vitamin C | 0.1 |
| Total Phase A | 77.5 |
| Phase B Botanical Blend | |
| Alcohol denatured | 10 |
| Zemea ® propanediol | 2 |
| Ethyl Hexyl Glycerin | 1 |
| Caprylil Capril Triglyceride | 2 |
| Sytenol ® | 0.5 |
| Benzyl alcohol | 1 |
| Salicylic acid | 2 |
| Decanediol | 0.5 |
| Farnesol | 0.3 |
| Bisabolol | 0.1 |
| Phenoxyethanol | 0.7 |
| Pomegranate oil | 0.5 |
| Thymol | 0.1 |
| Menthol | 0.1 |
| Rosemary oil | 0.1 |
| orange oil | 0.2 |
| Vetiver oil | 0.02 |
| Sorbitan monolaurate | 0.5 |
| Resveratrol | 0.5 |
| CHG (20%) | 0.25 |
| red sandalwood extract | 0.1 |
| silicone Shinetsu KF6038 | 0.5 |
| Total Phase B | 22.47 |

FGZB Spot Gel B3 Topical Gel

| Ingredient | % w/w |
|---|---|
| Deionized Water | Q.S. to 100 |
| Zinc gluconate | 0.2 |
| Zinc lactate | 0.2 |

-continued

FGZB Spot Gel B3 Topical Gel

| Ingredient | % w/w |
|---|---|
| Aloe powder | 0.2 |
| Glycolic acid | 0.5 |
| Lactic acid | 0.2 |
| BTMSCB emulsifier | 2.5 |
| Polawax ™ emulsifier | 2.5 |
| Jojoba oil | 2 |
| Cool to 30-40° C. | |
| HPMCSE polymer (1%) | 50 |
| Chitosan polymer (3%) | 10 |
| Calendula extract | 0.2 |
| 1,3 propanediol | 7 |
| Caprylil capril triglyceride | 2 |
| Ethyl hexyl glycerin | 1 |
| Benzyl alcohol | 1 |
| Salicylic acid | 2 |
| Decanediol | 0.5 |
| Bisabolol | 0.1 |
| Bakuchiol | 0.5 |
| Pomegranate Extract | 0.5 |
| Rosemary oil | 0.1 |
| Thymol | 0.1 |
| Menthol | 0.1 |
| Orange oil | 0.2 |
| Vetiver oil | 0.02 |
| Resveratrol | 0.5 |
| Red sandalwood extract | 0.1 |
| Chlorhexidine gluconate (20%) | 0.25 |
| Silicone Shin Etsu ® KF6038 | 1 |

FGZB Spot Gel B4 Topical Gel

| Ingredient | % w/w |
|---|---|
| Deionized Water | Q.S. to 100 |
| Zinc gluconate | 0.2 |
| Zinc lactate | 0.2 |
| Aloe powder | 0.2 |
| Glycolic acid | 0.5 |
| Lactic acid | 0.2 |
| BTMSCB emulsifier | 2.5 |
| Polawax ™ emulsifier | 2.5 |
| Jojoba oil | 2 |
| Cool to 30-40° C. | |
| HPMCSE polymer (1%) | 50 |
| Chitosan polymer (3%) | 10 |
| Calendula extract | 0.2 |
| 1,3 propanediol | 7 |
| Butylene glycol | 2 |
| Ethyl hexyl glycerin | 1 |
| Benzyl alcohol | 1 |
| Bakuchiol | 0.5 |
| Decanediol | 0.5 |
| Bisabolol | 0.1 |
| Pomegranate extract | 0.5 |
| Rosemary oil | 0.1 |
| Thymol | 0.1 |
| Menthol | 0.1 |
| Orange oil | 0.2 |
| Vetiver oil | 0.1 |
| Resveratrol | 0.2 |
| Red sandalwood extract | 0.02 |
| Chlorhexidine gluconate (20%) | 0.25 |
| Silicone Shin Etsu ® KF 6038 | Qs to 100 1 |

FGZB Spot Gel B5 Topical Gel

| Ingredient | % w/w |
|---|---|
| Phase A (50-60) | |
| Water | 13.53 |
| Zinc lactate | 0.2 |
| Zinc gluconate | 0.2 |
| Lactic acid | 0.2 |
| Glycolic acid | 0.5 |
| Aloe 100X | 0.2 |
| BTMSCB | 2 |
| Polawax ™ NF | 2 |
| Cupuacu Butter | 2 |
| Cool to 30-40° C. | |
| Phase B | |
| Sangelose ® 90 L 1% | 52 |
| Add Phase B to Phase A | |
| Chitosan 3% | 10 |
| Calendula extract (100%/oil) | 1 |
| Total Phase A + B | 83.83 |
| Phase C Botanical Blend | |
| Zemea ® propanediol | 5 |
| Ethyl Hexyl Glycerin | 1 |
| butylene glycol | 3 |
| Benzyl alcohol | 0.5 |
| salicylic acid | 2 |
| Bisabolol | 0.1 |
| Bakuchiol | 0.5 |
| Decanediol | 0.5 |
| Farnesol | 0.3 |
| Pomegranate oil | 0.5 |
| Rosemary oil | 0.1 |
| Orange oil | 0.1 |
| Vetiver oil | 0.02 |
| CHG (20%) | 0.25 |
| Vitamin E | 0.2 |
| Red sandalwood extract | 0.1 |
| Resveratrol BT | 0.5 |
| White tea extract | 0.5 |
| Silicone KF6038 | 1.0 |
| Total Phase C | 16.17 |

FGZB Spot Gel B5-A Topical Gel

| Ingredient | % w/w |
|---|---|
| Phase A (50-60) | |
| Water | 16.53 |
| Zinc lactate | 0.2 |
| Zinc gluconate | 0.2 |
| Lactic acid | 0.2 |
| Glycolic acid | 0.5 |
| Aloe 100X | 0.2 |
| BTMSCB | 2 |
| Polawax ™ NF | 2 |
| Cool to 30-40° C. | |
| Phase B | |
| Sangelose ® 90 L 1% | 52 |
| Add Phase B to Phase A | |
| Chitosan 3% | 10 |
| Calendula extract (100%/oil) | 1 |
| Total Phase A + B | 84.83 |
| Phase C Botanical Blend | |
| Zemea ® propanediol | 5 |
| Ethyl Hexyl Glycerin | 1 |
| butylene glycol | 3 |
| Benzyl alcohol | 0.5 |

-continued

FGZB Spot Gel B5-A Topical Gel

| Ingredient | % w/w |
| --- | --- |
| salicylic acid | 2 |
| Bisabolol | 0.1 |
| Bakuchiol | 0.5 |
| Decanediol | 0.5 |
| Farnesol | 0.3 |
| Pomegranate oil | 0.5 |
| Rosemary oil | 0.1 |
| Orange oil | 0.1 |
| Vetiver oil | 0.02 |
| CHG (20%) | 0.25 |
| Vitamin E | 0.2 |
| Red sandalwood extract | 0.1 |
| Resveratrol BT | 0.5 |
| White tea extract | 0.5 |
| Total Phase C | 15.17 |

FGZB Spot Gel B5-B Topical Gel

| Ingredient | % w/w |
| --- | --- |
| Phase A (50-60) | |
| Water | 17.03 |
| Zinc lactate | 0.2 |
| Zinc gluconate | 0.2 |
| Lactic acid | 0.2 |
| Glycolic acid | 0.5 |
| Aloe 100X | 0.2 |
| BTMSCB | 2 |
| Polawax ™ NF | 2 |
| Cool to 30-40° C. | |
| Phase B | |
| Sangelose ® 90 L 1% | 52 |
| Add Phase B to Phase A | |
| Chitosan 3% | 10 |
| Calendula extract (100%/oil) | 1 |
| Total Phase A + B | 85.33 |
| Phase C Botanical Blend | |
| Zemea ® propanediol | 5 |
| Ethyl Hexyl Glycerin | 1 |
| butylene glycol | 3 |
| Benzyl alcohol | 0.5 |
| salicylic acid | 2 |
| Bisabolol | 0.1 |
| Decanediol | 0.5 |
| Farnesol | 0.3 |
| Pomegranate oil | 0.5 |
| Rosemary oil | 0.1 |
| Orange oil | 0.1 |
| Vetiver oil | 0.02 |
| CHG (20%) | 0.25 |
| Vitamin E | 0.2 |
| Red sandalwood extract | 0.1 |
| Resveratrol BT | 0.5 |
| White tea extract | 0.5 |
| Total Phase C | 14.67 |

FGZB Spot Gel B6 Topical Gel

| Ingredient | % w/w |
| --- | --- |
| Phase A (50-60) | |
| Water | 12.53 |
| Zinc lactate | 0.2 |
| Zinc gluconate | 0.2 |
| Lactic acid | 0.2 |
| Glycolic acid | 0.5 |
| Aloe 100X | 0.2 |
| BTMSCB | 2.0 |
| Polawax ™ NF | 2.5 |
| Cupuacu Butter | 2.5 |
| Cool to 30-40° C. | |
| Phase B | |
| Sangelose ® 90 L 1% | 52 |
| Add Phase B to Phase A | |
| Chitosan 3% | 10 |
| Calendula extract (100%/oil) | 1 |
| Total Phase A + B | 83.83 |
| Phase C Botanical Blend | |
| Zemea ® propanediol | 5 |
| Ethyl Hexyl Glycerin | 1 |
| butylene glycol | 3 |
| Benzyl alcohol | 0.5 |
| salicylic acid | 2 |
| Bisabolol | 0.1 |
| Bakuchiol | 0.5 |
| Decanediol | 0.5 |
| Farnesol | 0.3 |
| Pomegranate oil | 0.5 |
| Rosemary oil | 0.1 |
| Orange oil | 0.1 |
| Vetiver oil | 0.02 |
| CHG (20%) | 0.25 |
| Vitamin E | 0.2 |
| Red sandalwood extract | 0.1 |
| Resveratrol BT | 0.5 |
| White tea extract | 0.5 |
| Silicone KF6038 | 1.0 |
| Total Phase C | 16.17 |

FGZB Spot Gel B6-A Topical Gel

| Ingredient | % w/w |
| --- | --- |
| Phase A (50-60) | |
| Water | 15.53 |
| Zinc lactate | 0.2 |
| Zinc gluconate | 0.2 |
| Lactic acid | 0.2 |
| Glycolic acid | 0.5 |
| Aloe 100X | 0.2 |
| BTMSCB | 2.5 |
| Polawax ™ NF | 2.5 |
| Cool to 30-40° C. | |
| Phase B | |
| Sangelose ® 90 L 1% | 52 |
| Add Phase B to Phase A | |
| Chitosan 3% | 10 |
| Calendula extract (100%/oil) | 1 |
| Total Phase A + B | 84.83 |
| Phase C Botanical Blend | |
| Zemea ® propanediol | 5 |
| Ethyl Hexyl Glycerin | 1 |
| butylene glycol | 3 |
| Benzyl alcohol | 0.5 |

FGZB Spot Gel B6-A Topical Gel

| Ingredient | % w/w |
|---|---|
| salicylic acid | 2 |
| Bisabolol | 0.1 |
| Bakuchiol | 0.5 |
| Decanediol | 0.5 |
| Farnesol | 0.3 |
| Pomegranate oil | 0.5 |
| Rosemary oil | 0.1 |
| Orange oil | 0.1 |
| Vetiver oil | 0.02 |
| CHG (20%) | 0.25 |
| Vitamin E | 0.2 |
| Red sandalwood extract | 0.1 |
| Resveratrol BT | 0.5 |
| White tea extract | 0.5 |
| Total Phase C | 15.17 |

FGZB Spot Gel B6-B Topical Gel

| Ingredient | % w/w |
|---|---|
| Phase A (50-60) | |
| Water | 16.03 |
| Zinc lactate | 0.2 |
| Zinc gluconate | 0.2 |
| Lactic acid | 0.2 |
| Glycolic acid | 0.5 |
| Aloe 100X | 0.2 |
| BTMSCB | 2.5 |
| Polawax ™ NF | 2.5 |
| Cool to 30-40° C. | |
| Phase B | |
| Sangelose ® 90 L 1% | 52 |
| Add Phase B to Phase A | |
| Chitosan 3% | 10 |
| Calendula extract (100%/oil) | 1 |
| Total Phase A + B | 85.33 |
| Phase C Botanical Blend | |
| Zemea ® propanediol | 5 |
| Ethyl Hexyl Glycerin | 1 |
| butylene glycol | 3 |
| Benzyl alcohol | 0.5 |
| salicylic acid | 2 |
| Bisabolol | 0.1 |
| Decanediol | 0.5 |
| Farnesol | 0.3 |
| Pomegranate oil | 0.5 |
| Rosemary oil | 0.1 |
| Orange oil | 0.1 |
| Vetiver oil | 0.02 |
| CHG (20%) | 0.25 |
| Vitamin E | 0.2 |
| Red sandalwood extract | 0.1 |
| Resveratrol BT | 0.5 |
| White tea extract | 0.5 |
| Total Phase C | 14.67 |

FGZB Spot Gel B7 Topical Gel

| Ingredient | % w/w |
|---|---|
| Phase A (50-60) | |
| Water | 14.53 |
| Zinc lactate | 0.2 |
| Zinc gluconate | 0.2 |
| Lactic acid | 0.2 |
| Glycolic acid | 0.5 |
| Aloe 100X | 0.2 |
| BTMSCB | 2 |
| Polawax ™ NF | 2 |
| Cupuacu Butter | 2 |
| Cool to 30-40° C. | |
| Phase B | |
| Sangelose ® 90 L 1% | 52 |
| Add Phase B to Phase A | |
| Chitosan 3% | 10 |
| Calendula extract (100%/oil) | 1 |
| Total Phase A + B | 84.83 |
| Phase C Botanical Blend | |
| Zemea ® propanediol | 5 |
| Ethyl Hexyl Glycerin | 1 |
| butylene glycol | 3 |
| Benzyl alcohol | 0.5 |
| salicylic acid | 2 |
| Bisabolol | 0.1 |
| Bakuchiol | 0.5 |
| Decanediol | 0.5 |
| Farnesol | 0.3 |
| Pomegranate oil | 0.5 |
| Rosemary oil | 0.1 |
| Orange oil | 0.1 |
| Vetiver oil | 0.02 |
| CHG (20%) | 0.25 |
| Vitamin E | 0.2 |
| Red sandalwood extract | 0.1 |
| Resveratrol BT | 0.5 |
| White tea extract | 0.5 |
| Total Phase C | 15.17 |

| Ingredient | % w/w |
|---|---|
| Phase A (65-70) | |
| Water | 39.65 |
| Zinc Lactate | 0.4 |
| Zinc Gluconate | 0.4 |
| Panthenol | 0.5 |
| EDTA | 0.1 |
| hydroxyethylcellulose | 2 |
| BTMSCB | 0.5 |
| Polawax ™ NF | 0.5 |
| Sangelose ® 90L (1%) | 30 |
| Aloe 100X | 1 |
| Calendula 100% Concentrate | 0.5 |
| Total Phase A + B | 75.55 |
| NaOH (10N) | 1 |
| Phase B Botanical Blend | |
| Benzoic acid | 0.2 |
| Thymol | 0.1 |
| Zemea ® propanediol | 3 |
| Ethyl Hexyl Glycerin | 1 |
| Benzyl alcohol | 1 |
| Salicylic acid | 2 |
| Sytenol ® | 0.5 |
| Farnesol | 0.5 |
| Grapefruit seed extract | 0.5 |
| Lemon extract | 0.5 |

-continued

| Ingredient | % w/w |
|---|---|
| Tea tree oil (lemon scented) | 1 |
| Green Tea Extract | 1 |
| Licorice extract | 0.5 |
| Red Sandalwood | 0.15 |
| Resveratrol | 1 |
| Frankincense oil | 0.5 |
| SDA-40B | 10 |
| Total Phase B | 23.45 |
| | 100 |

| Ingredient | % w/w |
|---|---|
| Phase A (65-70) | |
| Water | 36.1 |
| Zinc Lactate | 0.4 |
| Zinc Gluconate | 0.4 |
| Panthenol | 0.5 |
| EDTA | 0.1 |
| hydroxyethylcellulose | 2 |
| BTMSCB | 0.5 |
| Polawax ™ NF | 0.5 |
| Sangelose ® 90L (1%) | 30 |
| Aloe 100X | 1 |
| Calendula 100% Concentrate | 1.5 |
| Total Phase A + B | 73 |
| NaOH (10N) | 1 |
| Phase B Botanical Blend | |
| Benzoic acid | 0.2 |
| Thymol | 0.15 |
| Zemea ® propanediol | 3 |
| Ethyl Hexyl Glycerin | 1 |
| Benzyl alcohol | 1 |
| Salicylic acid | 2 |
| Sytenol ® | 0.5 |
| Farnesol | 0.5 |
| Grapefruit seed extract | 0.5 |
| Lemon extract | 0.5 |
| Tea tree oil (regular) | 1 |
| Tea tree oil (lemon scented) | 1 |
| Green Tea Extract | 1 |
| Licorice extract | 2 |
| Red Sandalwood | 0.15 |
| Resveratrol | 1 |
| Frankincense oil | 0.5 |
| SDA-40B | 10 |
| Total Phase B | 26 |
| | 100 |

| Ingredient | % w/w |
|---|---|
| Phase A (65-70) | |
| Water | 35.6 |
| Zinc Lactate | 0.4 |
| Zinc Gluconate | 0.4 |
| Panthenol | 0.5 |
| EDTA | 0.1 |
| BTMSCB | 0.5 |
| Polawax ™ NF | 0.5 |

-continued

| Ingredient | % w/w |
|---|---|
| Aloe 100X | 1 |
| hydroxyethylcellulose | 2.5 |
| Sangelose ® 90L (1%) | 30 |
| Calendula 100% Concentrate | 1.5 |
| Total Phase A + B | 73 |
| NaOH (10N) | 1 |
| Phase B Botanical Blend | |
| Benzoic acid | 0.2 |
| Thymol | 0.15 |
| Zemea ® propanediol | 3 |
| Ethyl Hexyl Glycerin | 1 |
| Benzyl alcohol | 1 |
| Salicylic acid | 2 |
| Sytenol ® | 0.5 |
| Farnesol | 0.5 |
| Grapefruit seed extract | 0.5 |
| Lemon extract | 0.5 |
| Tea tree oil (unscented) | 0.75 |
| Tea tree oil (lemon scented) | 1.25 |
| Green Tea Extract | 1 |
| Licorice extract | 2 |
| Red Sandalwood | 0.15 |
| Resveratrol | 1 |
| Frankincense oil | 0.5 |
| SDA-40B | 10 |
| Total Phase B | 26 |
| | 100 |

| Ingredient | % w/w |
|---|---|
| Phase A (65-70) | |
| Water | 35.7 |
| Zinc Lactate | 0.4 |
| Zinc Gluconate | 0.4 |
| Panthenol | 0.5 |
| EDTA | 0.1 |
| BTMSCB | 0.5 |
| Polawax ™ NF | 0.5 |
| Aloe 100X | 1 |
| hydroxyethylcellulose | 2.2 |
| Sangelose ® 90L (1%) | 30 |
| Calendula 100% Concentrate | 1.5 |
| Total Phase A + B | 72.8 |
| NaOH (10N) | 1.2 |
| Phase B Botanical Blend | |
| Benzoic acid | 0.20 |
| Thymol | 0.15 |
| Zemea ® propanediol | 3 |
| Ethyl Hexyl Glycerin | 1 |
| Benzyl alcohol | 1 |
| Salicylic acid | 2 |
| Sytenol ® | 0.5 |
| Farnesol | 0.5 |
| Grapefruit seed extract | 0.5 |
| Lemon extract | 0.5 |
| Tea tree oil (unscented) | 0.5 |
| Tea tree oil (lemon scented) | 1.25 |
| Green Tea Extract | 1 |
| Licorice extract | 2 |
| Red Sandalwood | 0.15 |
| Resveratrol | 1 |
| Frankincense oil | 0.75 |
| SDA-40B | 10 |
| Total Phase B | 26 |
| | 100 |

| Ingredient | % w/w |
|---|---|
| Phase A (65-70) | |
| Water | 37.7 |
| Zinc Lactate | 0.4 |
| Zinc Gluconate | 0.4 |
| Panthenol | 0.5 |
| EDTA | 0.1 |
| BTMSCB | 0.5 |
| Polawax ™ NF | 0.5 |
| hydroxyethylcellulose | 2.2 |
| Aloe 100X | 1 |
| Sangelose ® 90L (1%) | 30 |
| Calendula 100% Concentrate | 0.5 |
| Total Phase A + B | 73.8 |
| NaOH (10N) | 1.2 |
| Phase B Botanical Blend | |
| Benzoic acid | 0.2 |
| Thymol | 0.15 |
| Zemea ® propanediol | 3 |
| Ethyl Hexyl Glycerin | 1 |
| Benzyl alcohol | 1 |
| Salicylic acid | 2 |
| Sytenol ® | 0.5 |
| Farnesol | 0.5 |
| Grapefruit seed extract | 0.5 |
| Lemon extract | 0.5 |
| Tea tree oil (unscented) | 0.5 |
| Tea tree oil (lemon scented) | 1.25 |
| Green Tea Extract | 1 |
| Licorice extract | 1 |
| Red Sandalwood | 0.15 |
| Resveratrol | 1 |
| Frankincense oil | 0.75 |
| SDA-40B | 10 |
| Total Phase B | 25 |
| | 100 |

| Ingredient | % w/w |
|---|---|
| Phase A (65-70) | |
| Water | 38.7 |
| Zinc Lactate | 0.4 |
| Zinc Gluconate | 0.4 |
| Panthenol | 0.5 |
| EDTA | 0.1 |
| BTMSCB | 0.5 |
| Polawax ™ NF | 0.5 |
| hydroxyethylcellulose | 2.2 |
| Aloe 100X | 1 |
| Sangelose ® 90L (1%) | 30 |
| Calendula 100% Concentrate | 0.5 |
| Total Phase A + B | 73.8 |
| NaOH (10N) | 1.2 |
| Phase B Botanical Blend | |
| Benzoic acid | 0.2 |
| Thymol | 0.15 |
| Zemea ® propanediol | 3 |
| Ethyl Hexyl Glycerin | 1 |
| Benzyl alcohol | 1 |
| Salicylic acid | 2 |
| Farnesol | 0.5 |
| Lemon extract | 0.5 |
| Tea tree oil (unscented) | 0.5 |
| Tea tree oil (lemon scented) | 1.25 |

-continued

| Ingredient | % w/w |
|---|---|
| Green Tea Extract | 1 |
| Licorice extract | 1 |
| Red Sandalwood | 0.15 |
| Resveratrol | 1 |
| Frankincense oil | 0.75 |
| SDA-40B | 10 |
| Total Phase B | 25 |
| | 100 |

| Ingredient | % w/w |
|---|---|
| Phase A (65-70) | |
| Water | 37.5 |
| Zinc Lactate | 0.4 |
| Zinc Gluconate | 0.4 |
| Panthenol | 0.5 |
| EDTA | 0.1 |
| BTMSCB | 0.5 |
| Polawax ™ NF | 0.5 |
| hydroxyethylcellulose | 2.2 |
| Xanthan Gum | 0.5 |
| Aloe 100X | 1 |
| Sangelose ® 90L (1%) | 30 |
| Calendula 100% Concentrate | 0.5 |
| Total Phase A + B | 73.8 |
| NaOH (10N) | 1.2 |
| Phase B Botanical Blend | |
| Benzoic acid | 0.2 |
| Thymol | 0.15 |
| Zemea ® propanediol | 3 |
| Ethyl Hexyl Glycerin | 1 |
| Benzyl alcohol | 1 |
| Salicylic acid | 2 |
| Sytenol ® | 0.5 |
| Farnesol | 0.5 |
| Grapefruit seed extract | 0.5 |
| Lemon extract | 0.5 |
| Tea tree oil (unscented) | 0.5 |
| Tea tree oil (lemon scented) | 1.25 |
| Green Tea Extract | 1 |
| Licorice extract | 1 |
| Red Sandalwood | 0.15 |
| Resveratrol | 1 |
| Frankincense oil | 0.75 |
| SDA-40B | 10 |
| Total Phase B | 25 |
| | 100 |

| Ingredient | % w/w |
|---|---|
| Phase A (65-70) | |
| Water | 37.2 |
| Zinc Lactate | 0.4 |
| Zinc Gluconate | 0.4 |
| Panthenol | 0.5 |
| EDTA | 0.1 |
| BTMSCB | 0.5 |
| Polawax ™ NF | 0.5 |

-continued

| Ingredient | % w/w |
|---|---|
| hydroxyethylcellulose | 2.2 |
| Aloe 100X | 1 |
| Sangelose ® 90L (1%) | 30 |
| Calendula 100% Concentrate | 0.5 |
| Total Phase A + B | 73.8 |
| NaOH (10N) | 1.2 |
| Phase B Botanical Blend | |
| Benzoic acid | 0.2 |
| Thymol | 0.15 |
| Zemea ® propanediol | 3 |
| Ethyl Hexyl Glycerin | 1 |
| Benzyl alcohol | 1 |
| Benzoyl Peroxide | 2.5 |
| Sytenol ® | 0.5 |
| Farnesol | 0.5 |
| Grapefruit seed extract | 0.5 |
| Lemon extract | 0.5 |
| Tea tree oil (unscented) | 0.5 |
| Tea tree oil (lemon scented) | 1.25 |
| Green Tea Extract | 1 |
| Licorice extract | 1 |
| Red Sandalwood | 0.15 |
| Resveratrol | 1 |
| Frankincense oil | 0.75 |
| SDA-40B | 10 |
| Total Phase B | 25.5 |
| | 100 |

| Ingredient | % w/w |
|---|---|
| Phase A (65-70) | |
| Water | 37.7 |
| Zinc Lactate | 0.4 |
| Zinc Gluconate | 0.4 |
| Panthenol | 0.5 |
| EDTA | 0.1 |
| BTMSCB | 0.5 |
| Polawax ™ NF | 0.5 |
| hydroxyethylcellulose | 2.2 |
| Aloe 100X | 1 |
| Sangelose ® 90L (1%) | 30 |
| Calendula 100% Concentrate | 0.5 |
| Total Phase A + B | 73.8 |
| NaOH (10N) | 1.2 |
| Phase B Botanical Blend | |
| Benzoic acid | 0.2 |
| Thymol | 0.15 |
| Zemea ® propanediol | 3 |
| Ethyl Hexyl Glycerin | 1 |
| Benzyl alcohol | 1 |
| Salicylic Acid | 1 |
| Benzoyl Peroxide | 1 |
| Sytenol ® | 0.5 |
| Farnesol | 0.5 |
| Grapefruit seed extract | 0.5 |
| Lemon extract | 0.5 |
| Tea tree oil (unscented) | 0.5 |
| Tea tree oil (lemon scented) | 1.25 |
| Green Tea Extract | 1 |

-continued

| Ingredient | % w/w |
|---|---|
| Licorice extract | 1 |
| Red Sandalwood | 0.15 |
| Resveratrol | 1 |
| Frankincense oil | 0.75 |
| SDA-40B | 10 |
| Total Phase B | 25 |
| | 100 |

| Acne Scar Removal Serum (SR-6) | |
|---|---|
| Ingredient | % w/w |
| Aloe gel | 60 |
| Lemon extract | 5 |
| Almond oil | 10 |
| Glycerin | 6.3 |
| Panthenol | 0.5 |
| Zemea ® propanediol | 5 |
| Tween ® 20 | 1 |
| Helichrysum oil | 0.5 |
| Calendula oil | 0.5 |
| Frankincense oil | 0.5 |
| Broccoli seed oil | 0.5 |
| Raspberry seed oil | 0.3 |
| Pomegranate seed oil | 0.4 |
| Tomato Seed Oil | 5 |
| Vitamin E | 2.5 |
| Neroli oil | 0.5 |
| Geranium oil | 0.5 |
| Lavender oil | 0.5 |
| Cedarwood oil | 0.5 |
| Total | 100 |

| Acne Scar Removal Serum (SR-6B) | |
|---|---|
| Ingredient | % w/w |
| BTMSCB | 0.1 |
| Polawax ™ | 0.1 |
| Zinc gluconate | 0.1 |
| Aloe gel | 49.2 |
| Sangelose ® (1%) | 10 |
| Lemon extract | 5 |
| Almond oil | 10 |
| Glycerin | 6.3 |
| Panthenol | 0.5 |
| Zemea ® propanediol | 5 |
| Tween ® 20 | 1 |
| Helichrysum oil | 0.5 |
| Calendula oil | 0.5 |
| Frankincense oil | 0.5 |
| Broccoli seed oil | 0.5 |
| Raspberry seed oil | 0.3 |
| Pomegranate seed oil | 0.4 |
| Tomato Seed Oil | 5 |
| Vitamin E | 2.5 |
| Neroli oil | 0.5 |
| Geranium oil | 0.5 |
| Lavender oil | 0.5 |
| Cedarwood oil | 0.5 |
| Salicylic Acid | 0.5 |
| Total | 100 |

Acne Scar Removal Serum (SR-7)

| Ingredient | % w/w |
| --- | --- |
| Almond oil | 10 |
| Sunflower oil | 8 |
| BTMSCB | 0.1 |
| Polawax ™ | 0.1 |
| Zinc gluconate | 0.1 |
| Aloe gel | 50 |
| Sangelose ® (1%) | 10 |
| Lemon extract | 5 |
| Zemea ® propanediol | 4.5 |
| Panthenol | 0.5 |
| Tween ® 20 | 1 |
| Helichrysum oil | 0.5 |
| Calendula oil | 0.5 |
| Frankincense oil | 0.5 |
| Broccoli seed oil | 0.5 |
| Raspberry seed oil | 0.3 |
| Pomegranate seed oil | 0.4 |
| Tomato Seed Oil | 5 |
| Vitamin E | 1 |
| Neroli oil | 0.5 |
| Myrrh | 0.5 |
| Cedarwood oil | 0.5 |
| Salicylic Acid | 0.5 |
| Total | 100 |

Acne Scar Removal Serum (SR-8)

| Ingredient | % w/w |
| --- | --- |
| Almond oil | 8 |
| Coconut oil | 5 |
| BTMSCB | 0.1 |
| Polawax ™ | 0.1 |
| Zinc gluconate | 0.2 |
| Aloe gel | 50 |
| Sangelose ® (1%) | 10 |
| Lemon extract | 5 |
| Sunflower seed oil | 5 |
| Honey | 5 |
| Helichrysum oil | 0.5 |
| Calendula oil | 0.5 |
| Frankincense oil | 0.5 |
| Tea tree oil | 0.5 |
| Panthenol | 0.5 |
| Pomegranate seed oil | 0.3 |
| Tomato Seed Oil | 5 |
| Vitamin E | 1 |
| Sorbitan Oleate (Tween ® 20) | 1 |
| Myrrh | 0.3 |
| Cedarwood oil | 0.5 |
| Salicylic acid | 0.5 |
| Neroli | 0.25 |
| Geranium | 0.25 |
| Total | 100 |

Acne Scar Removal Serum (SR-8B)

| Ingredient | % w/w |
| --- | --- |
| Almond oil | 7.7 |
| Coconut oil | 5 |
| BTMSCB | 0.1 |
| Polawax ™ | 0.1 |
| Zinc gluconate | 0.2 |
| Aloe gel | 50 |
| Xanthan gum | 0.3 |
| Sangelose ® (1%) | 10 |
| Lemon extract | 5 |

-continued

Acne Scar Removal Serum (SR-8B)

| Ingredient | % w/w |
| --- | --- |
| Sunflower seed oil | 5 |
| Honey | 5 |
| Helichrysum oil | 0.5 |
| Calendula oil | 0.5 |
| Frankincense oil | 0.5 |
| Tea tree oil | 0.5 |
| Panthenol | 0.5 |
| Pomegranate seed oil | 0.3 |
| Tomato Seed Oil | 5 |
| Vitamin E | 1 |
| Sorbitan Oleate (Tween ® 20) | 1 |
| Myrrh | 0.3 |
| Cedarwood oil | 0.5 |
| Salicylic acid | 0.5 |
| Neroli | 0.25 |
| Geranium | 0.25 |
| Total | 100 |

FGZB Exfoliant Wipe Solution
Exfoliant Wipe Solution - EW3

| Ingredient | % w/w |
| --- | --- |
| Aloe gel (Carbopol ®) | 50 |
| Water | 16.8 |
| Zinc gluconate | 0.2 |
| Panthenol | 0.5 |
| Apple cider Vinegar | 10 |
| Rosewater | 5 |
| Lemon extract | 5 |
| Tea tree oil | 0.5 |
| Tween ® 20 | 1 |
| Zemea ® propanediol | 10 |
| Salicylic acid | 0.5 |
| Witch hazel Distillate | 1 |
| Total | 100 |

Exfoliant Wipe Solution - EW4

| Ingredient | % w/w |
| --- | --- |
| Aloe gel (Carbopol ®) | 40 |
| Water | 16.8 |
| Zinc gluconate | 0.2 |
| Panthenol | 0.5 |
| Apple cider Vinegar | 10 |
| Rosewater | 5 |
| Lemon extract | 5 |
| Tea tree oil | 0.5 |
| Tween ® 20 | 1 |
| Salicylic acid | 0.5 |
| Glycerin | 10 |
| Sangelose ® (1%) | 10 |
| BTMSCB | 0.5 |
| Polawax ™ | 0.5 |
| Witch hazel distillate | 1 |
| Total | 100 |

Exfoliant Wipe Solution - EW5

| Ingredient | % w/w |
| --- | --- |
| Water | 16.1 |
| Incroquat ™ | 0.1 |

-continued

Exfoliant Wipe Solution - EW5

| Ingredient | % w/w |
| --- | --- |
| Polawax ™ | 0.1 |
| Aloe gel (Carbopol ®) | 40 |
| Sangelose ® | 10 |
| Zinc gluconate | 0.2 |
| Panthenol | 0.5 |
| Apple cider Vinegar | 10 |
| Rosewater | 5 |
| Lemon extract | 5 |
| Tween ® 20 | 1 |
| Zemea ® propanediol | 10 |
| Salicylic Acid | 0.5 |
| Witch hazel Distillate | 1 |
| Tea tree oil | 0.5 |
| Total | 100 |

Exfoliant Wipe Solution - EW6

| Ingredient | % w/w |
| --- | --- |
| Water | 26.8 |
| Salicylic acid | 0.5 |
| Honey | 5 |
| Apple cider vinegar | 10 |
| Lemon extract | 0.5 |
| Rosewater | 5 |
| Tea tree oil (lemon scented) | 0.3 |
| Coconut oil | 5 |
| Panthenol | 0.5 |
| Aloe gel | 30 |
| Zinc gluconate | 0.2 |
| Panthenol | 0.5 |
| Sesame seed oil | 5 |
| Vitamin E | 0.5 |
| Sangelose ® (1%) | 10 |
| BTMSCB | 0.1 |
| Polawax ™ | 0.1 |
| Total | 100 |

Exfoliant Wipe Solution - EW7

| Ingredient | % w/w |
| --- | --- |
| Aloe gel (Carbopol ®) | 40 |
| Water | 14.8 |
| hydroxyethylcellulose | 0.5 |
| Panthenol | 0.5 |
| Zinc gluconate | 0.2 |
| Apple cider Vinegar | 10 |
| Rosewater | 5 |
| Lemon extract | 5 |
| Tea tree oil | 0.5 |
| Tween ® 20 | 1 |
| Salicylic acid | 0.5 |
| Glycerin | 10 |
| Sangelose ® (1%) | 10 |
| BTMSCB | 0.5 |
| Polawax ™ | 0.5 |
| Witch hazel distillate | 1 |
| Total | 100 |

Exfoliant Wipe Solution - EW7B

| Ingredient | % w/w |
| --- | --- |
| Aloe gel (Carbopol ®) | 40 |
| Water | 14.5 |
| hydroxyethylcellulose | 0.5 |
| Panthenol | 0.5 |
| Xanthan gum | 0.3 |
| Zinc gluconate | 0.2 |
| Apple cider Vinegar | 10 |
| Rosewater | 5 |
| Lemon extract | 5 |
| Tea tree oil | 0.5 |
| Tween ® 20 | 1 |
| Salicylic acid | 0.5 |
| Glycerin | 10 |
| Sangelose ® (1%) | 10 |
| BTMSCB | 0.5 |
| Polawax ™ | 0.5 |
| Witch hazel distillate | 1 |
| Total | 100 |

Acute Scar Removal Cream AS-1

| Ingredient | % w/w |
| --- | --- |
| BTMSCB | 0.5 |
| Polawax ™ | 0.5 |
| Sangelose ® (1%) | 10 |
| Salicylic acid | 0.5 |
| Panthenol | 0.5 |
| Zinc gluconate | 0.2 |
| Helichrysum oil | 0.5 |
| Frankincense oil | 0.5 |
| Rose hip oil | 0.3 |
| Neroli oil | 0.25 |
| Geranium oil | 0.25 |
| Almond oil | 10.5 |
| Jojoba oil | 8 |
| Apple cider vinegar | 5 |
| Aloe gel | 50 |
| Onion extract | 1 |
| Emu oil | 1 |
| Tea tree oil | 0.5 |
| Honey | 10 |
| Total | 100 |

AS-1B

| Ingredient | % w/w |
| --- | --- |
| BTMSCB | 0.5 |
| Polawax ™ | 0.5 |
| Sangelose ® (1%) | 10 |
| Xanthan Gum | 0.3 |
| Salicylic acid | 0.5 |
| Panthenol | 0.5 |
| Zinc gluconate | 0.2 |
| Helichrysum oil | 0.5 |
| Frankincense oil | 0.5 |
| Rose hip oil | 0.3 |
| Neroli oil | 0.25 |
| Geranium oil | 0.25 |
| Almond oil | 10.5 |
| Jojoba oil | 7.7 |
| Apple cider vinegar | 5 |

-continued

AS-1B

| Ingredient | % w/w |
|---|---|
| Aloe gel | 50 |
| Onion extract | 1 |
| Emu oil | 1 |
| Tea tree oil | 0.5 |
| Honey | 10 |
| Total | 100 |

Example 4

Comparison of Antibacterial Efficacy of FGZB Spot Gel and Other Spot Gel Formulations Containing Zinc Salts, Botanicals and Salicylic Acid Acne Cream 1 and 2

Acne Cream 1

| Ingredients | % WT |
|---|---|
| Salicylic acid (active) | 2% |
| Base ingredients | |
| WATER (AQUA) | Q.S to 100 |
| ALCOHOL DENATURED. | 10 |
| PROPYLENE GLYCOL | 1 |
| HYDROXYETHYLCELLULOSE | 2 |
| DIMETHYL ISOSORBIDE | 0.1 |
| ZINC GLUCONATE | 0.2 |
| ZINC LACTATE | 0.2 |
| PANTHENOL | 0.5 |
| PEG-8 (Polyethylene glycol) | 1 |
| ALOE BARBADENSIS LEAF EXTRACT | 0.01 |
| CAMELLIA OLEIFERA LEAF EXTRACT | 0.001 |
| BUTYLENE GLYCOL | 1 |
| COCOS NUCIFERA (COCONUT) WATER | 0.99 |
| WITHANIA SOMNIFERA FLOWER EXTRACT | 0.99 |
| PICHIA/RESVERATROL FERMENT EXTRACT | 0.5 |
| PHOSPHOLIPIDS | 0.0001 to 0.5 |
| RETINYL PALMITATE | 0.1 |
| ASCORBYL PALMITATE | 0.1 |
| TOCOPHERYL ACETATE | 0.1 |
| GLYCOLIC ACID | 0.5 |
| GLYCERIN | 1 |
| ETHYLHEXYLGLYCERIN | 0.2 to 3 |
| PHENOXYETHANOL | 0.99 |
| SODIUM HYDROXIDE | 0.5 |
| | 100% |

Acne Cream 2

| Ingredients | % WT |
|---|---|
| Deionized Water | Q.S. to 100 |
| Hydroxyethyl cellulose | 1 |
| Zinc Lactate | 0.2 |
| Zinc Gluconate | 0.2 |
| Glycolic Acid (70%) | 1.6 |
| Glycerin | 1 |
| 1,3 Butylene Glycol | 6 |
| Ritapan ® D | 0.5 |
| Deionized Water | 10 |
| KOH | 1.5 |
| SD Alcohol | 12 |
| Dimethyl Isosorbide | 5 |
| Symcalmin ® | 1 |
| Ethyl Hexyl Glycerin | 0.3 |
| Ritabate ® 20 | 4 |
| Farnesol | 0.3 |
| Phenoxyethanol | 0.7 |

-continued

Acne Cream 2

| Ingredients | % WT |
|---|---|
| Vitamin E Acetate | 0.01 |
| Vitamin A Palmitate | 0.01 |
| Vitamin C (BVOSC) | 0.01 |
| Chlorhexidine Gluconate | 0.2 |
| Benzalkonium chloride | 0.12 |
| White Tea Extract (BC) | 1 |
| Resveratrol (BC Research) | 1 |
| AFG 1224 Jaffa Orange | 0.5 |
| | 100 |

FGZB B-2 Topical Gel

| Ingredient | % w/w |
|---|---|
| Deionized Water | Q.S. to 100 |
| Zinc gluconate | 0.2 |
| Zinc lactate | 0.2 |
| Aloe powder | 0.2 |
| Hydroxy propyl methyl cellulose (Methocel ™) | 0.5 |
| Glycolic acid | 0.2 |
| Lactic acid | 0.2 |
| BTMSCB emulsifier | 2.5 |
| Polawax ™ emulsifier | 3 |
| HPMCSE polymer | 0.5 |
| Chitosan polymer | 0.15 |
| Calendula extract | 0.2 |
| Alcohol denatured | 10 |
| 1,3 propanediol | 2 |
| Caprylil capril triglyceride | 2 |
| Ethyl hexyl glycerin | 1 |
| Decanediol | 0.5 |
| Bisabolol | 0.1 |
| Pomegranate oil | 0.5 |
| Rosemary oil | 0.1 |
| Thymol | 0.1 |
| Menthol | 0.1 |
| Orange oil | 0.2 |
| Vetiver oil | 0.02 |
| Resveratrol | 0.5 |
| Red sandalwood extract | 0.1 |
| Chlorhexidine gluconate | QS to 100 |

TABLE 3

Table 3: Antibacterial efficacy of FGZB-B2 spot cream against *S. aureus*: comparison with other Acne cream products containing, salicylic acid

| Product | Zone of inhibition (mm) |
|---|---|
| Acne cream 1 | 15 |
| Acne cream 2 | 12 |
| FGZB -B2 | 18 |

49

Table 3
Conclusion: FGZB-1 Shows larger zone of inhibition against *S. aureus* which is also responsible for Acne pimples.

TABLE 4

| Table 4: Efficacy of FG ZB-B2 on 2 subjects after 7 to10 days of treatment | | |
| --- | --- | --- |
| | Volunteer 1 | Volunteer 2 |
| Percent reduction in size of the pimples | 50 | 80 |
| Percent reduction in pimples | 50 | 70 |
| Percent reduction in redness | 60 | 100 |

Table 4
Results showed 50 to 100 percent reduction in acne symptoms after only 7 to 10 days of treatment. Advantageously, no itching and/or burning sensation was reported in either of the volunteers.

Formulations containing salicylic acid have been shown to improve acne affected skin in 4-6 weeks. Our preliminary evaluation indicates that FGZB shows improvement in acne affected skin in 7-10 days.

Although the present invention has been described in relation to embodiments thereof, these embodiments and examples are merely exemplary and not intended to be limiting. Many other variations and modifications and other uses will become apparent to those skilled in the art. The present invention should, therefore, not be limited by the specific disclosure herein, and can be embodied in other forms not explicitly described here, without departing from the spirit thereof.

We claim:
1. A method of treating an acne related skin disorder, the method comprising contacting skin with an acne treatment composition that achieves more than 3 log 10 reduction of bacterial growth from control group within 15 second contact with acne causing bacteria,
   wherein the acne treatment composition is a film forming composition that comprises:
   a. a combination of 0.05 to 0.2% w/w rosemary oil, 0.3 to 1% w/w pomegranate extract, 0.2 to 2% w/w licorice extract, and 0.1 to 0.5% w/w orange oil;
   b. 0.5 to 2% w/w salicylic acid and 0.1 and to 1% w/w glycolic acid;
   c. 0.5 to 10% w/w of one or more emollient solvent selected from 1,3 propanediol, ethylhexylglycerin, butylene glycol, or any combination thereof;
   d. 0.1 to 3% w/w one or more polymer selected from hydroxypropyl cellulose, hydroxypropylmethyl cellulose, or any combination thereof; and
   e. 0.1 to 1% w/w one or more zinc salt selected from zinc gluconate, zinc lactate, or any combination thereof.
2. The method of claim 1, wherein the acne treatment composition further comprises Green tea extract, Calendula extract, Witch hazel extract, Aloe extract, Grapefruit seed extract, Basil oil, Jojoba oil, Tea tree oil, Vetiver oil, Red Sandalwood extract, Resveratrol, Vitamin E, Vitamin C or any combination thereof.
3. The method of claim 2, wherein the acne treatment composition further comprises one or more emulsifiers or one or more solubilizers.

* * * * *